United States Patent
Kim et al.

(10) Patent No.: US 11,730,698 B2
(45) Date of Patent: Aug. 22, 2023

(54) STABLE LIQUID PHARMACEUTICAL PREPARATION

(71) Applicant: CELLTRION INC., Incheon (KR)

(72) Inventors: So Young Kim, Incheon (KR); Yeon Kyeong Shin, Incheon (KR); Hye Young Kang, Incheon (KR); Kwang Woo Kim, Incheon (KR); Jun Seok Oh, Incheon (KR); Su Jung Kim, Incheon (KR); Joon Won Lee, Incheon (KR); Won Yong Han, Incheon (KR); Jae Bin Lee, Incheon (KR); Ji Won Roh, Incheon (KR); Ji Min Kwak, Incheon (KR)

(73) Assignee: CELLTRION INC., Incheon (KR)

(*) Notice: Subject to any disclaimer, the term of this patent is extended or adjusted under 35 U.S.C. 154(b) by 266 days.

(21) Appl. No.: 17/261,145

(22) PCT Filed: Jul. 18, 2019

(86) PCT No.: PCT/KR2019/008880
§ 371 (c)(1),
(2) Date: Jan. 18, 2021

(87) PCT Pub. No.: WO2020/017901
PCT Pub. Date: Jan. 23, 2020

(65) Prior Publication Data
US 2021/0315813 A1    Oct. 14, 2021

(30) Foreign Application Priority Data

Jul. 19, 2018 (KR) .................. 10-2018-0083856

(51) Int. Cl.
| | |
|---|---|
| *A61K 9/08* | (2006.01) |
| *A61K 9/19* | (2006.01) |
| *A61K 47/02* | (2006.01) |
| *A61K 47/10* | (2017.01) |
| *A61K 47/12* | (2006.01) |
| *A61K 47/18* | (2017.01) |
| *A61K 47/26* | (2006.01) |
| *C07K 16/32* | (2006.01) |

(52) U.S. Cl.
CPC ............... *A61K 9/08* (2013.01); *A61K 9/19* (2013.01); *A61K 47/02* (2013.01); *A61K 47/10* (2013.01); *A61K 47/12* (2013.01); *A61K 47/183* (2013.01); *A61K 47/26* (2013.01); *C07K 16/32* (2013.01)

(58) Field of Classification Search
CPC . A61K 9/08; A61K 9/19; A61K 47/02; A61K 47/10; A61K 47/12; A61K 47/183; A61K 47/26; A61K 2039/505; A61K 9/0019; A61K 39/001106; A61K 39/395; A61K 39/39591; A61K 39/3955; C07K 16/32; C07K 2317/94; C07K 16/241; C07K 16/4291
See application file for complete search history.

(56) References Cited

U.S. PATENT DOCUMENTS

| | | | |
|---|---|---|---|
| 4,861,335 A | 8/1989 | Reynolds | |
| 5,085,642 A | 2/1992 | Sarnoff et al. | |
| 5,681,291 A | 10/1997 | Galli | |
| 6,331,174 B1 | 12/2001 | Reinhard et al. | |
| 8,372,396 B2 | 2/2013 | Andya et al. | |
| 9,017,671 B2 | 4/2015 | Andya et al. | |
| 9,345,661 B2 | 5/2016 | Adler et al. | |
| 9,968,676 B2 | 5/2018 | Adler et al. | |
| 2005/0276802 A1* | 12/2005 | Adams ................... A61P 37/00 536/23.53 |
| 2010/0015157 A1* | 1/2010 | Andya ............. A61K 39/39541 424/139.1 |
| 2011/0044977 A1 | 2/2011 | Adler et al. | |
| 2012/0014968 A1 | 1/2012 | Walsh et al. | |
| 2015/0071925 A1* | 3/2015 | Larson .................. A61K 47/20 424/134.1 |
| 2016/0017029 A1 | 1/2016 | Walsh et al. | |
| 2016/0166689 A1* | 6/2016 | Adler ...................... A61P 35/04 424/133.1 |
| 2018/0100026 A1 | 4/2018 | Kim et al. | |
| 2018/0296470 A1 | 10/2018 | Eng-Wong et al. | |
| 2019/0010222 A1 | 1/2019 | Walsh et al. | |

FOREIGN PATENT DOCUMENTS

| | | |
|---|---|---|
| AU | 2013202020 | 4/2013 |
| KR | 10-2007-0068385 | 6/2007 |
| KR | 10-2013-0041374 | 4/2013 |
| KR | 10-2013-0079486 | 7/2013 |
| WO | WO 2011/012637 | 2/2011 |
| WO | WO 2016/168769 | 10/2016 |
| WO | WO 2018/136412 | 7/2018 |

OTHER PUBLICATIONS

EP, EP 19837708 Supp SR, Jul. 16, 2021, Celltrion Inc.
Hamizi et al., "Subcutaneous Trastuzumab: Development of a New Formulation for Treatment of HER2-Positive Early Breast Cancer", OncoTargets and Therapy vol. 6, Feb. 2013, New Zealand, pp. 89-94.
Kemter et al., "Amino Acid-Based Advanced Liquid Formulation Decelopment for Highly Concentrated Therapeutic Antibodies Balances Physical and Chemical Stability and Low Viscosity", Biotechnology Journal vol. 13, Jul. 2018, Germany, 13 pages.
WO, PCT/KR2019/008880 SR-WOw/Trans, Oct. 23, 2019, Celltrion Inc.

(Continued)

*Primary Examiner* — Robert A Wax
*Assistant Examiner* — Quanglong N Truong
(74) *Attorney, Agent, or Firm* — Wells St. John P.S.

(57) ABSTRACT

A stable liquid pharmaceutical formulation according to the present invention includes an antibody or antigen-binding fragment thereof, a surfactant, a sugar or a sugar derivative, a buffer, and a stabilizer. The stable liquid pharmaceutical formulation according to the present invention has low viscosity not only when antibody content is low but also when antibody content is high, and exhibits superior long-term storage stability based on superior stability observed under accelerated conditions and harsh conditions.

25 Claims, No Drawings
Specification includes a Sequence Listing.

(56) References Cited

OTHER PUBLICATIONS

GenBank, "anti-HER2 single chain antibody variable region, partial [synthetic construct]", NCBI GenBank Accession No. AIL24996.1, available online at https://www.ncbi.nlm.nih.gov/protein/AIL24996.1, Oct. 7, 2019, 2 pages.

GenBank, "Chain H, Trastuzumab Anti-HER2 Fab Heavy Chain", NCBI GenBank Accession No. 6BHZ_H, available online at https://www.ncbi.nim.nih.gov/protein/6BHZ_H, Oct. 7, 2019, 3 pages.

GenBank, "Chain L, Trastuzumab Anti-HER2 Fab Light Chain D185A", NCBI GenBank Accession No. 6BHZ_L, available online at https://www.ncbi.nlm.nih.gov/protein/6BHZ_L, Oct. 7, 2019, 3 pages.

\* cited by examiner

STABLE LIQUID PHARMACEUTICAL PREPARATION

RELATED PATENT DATA

This application is a 35 U.S.C. § 371 of and claims priority to PCT International Application No. PCT/KR2019/008880, filed 18 Jul. 2019, which claims priority to KR Application No. 10-2018-0083856, filed 19 Jul. 2018, each of which is incorporated herein by reference.

This patent incorporates by reference the material in the sequence listing .txt file submitted in computer readable form. The text file is titled HA153-003.txt. This file was created Jan. 14, 2021 and is 9.26 KB.

TECHNICAL FIELD

The present invention relates to a stable liquid pharmaceutical formulation.

BACKGROUND ART

Human epidermal growth factor receptor 2 (HER2) is a tyrosine-phosphorylating enzyme that binds to the surface of cell membranes, and is known to be involved in a signaling pathway that causes cell growth and cell differentiation, and also to be involved in cell malignancy upon overexpression or activation. Overexpression of HER2 protein is one of the prognostic factors of breast cancer, leading to higher disease recurrence and worse prognosis. The overexpression of HER2 protein may be inhibited using a targeted therapeutic agent, thereby making it possible to treat diseases such as breast cancer, rectal cancer and gastrointestinal cancer.

Trastuzumab is a monoclonal antibody capable of functioning as a HER2 expression inhibitor. Conventional formulations using this antibody are prepared in the form of a freeze-dried powder, reconstituted, and intravenously injected depending on the administration method and dose of each disease, or are prepared in the form of a liquid and subcutaneously injected. However, the conventional method of administration of such a formulation (freeze drying→reconstitution→intravenous administration) is expensive and cumbersome and causes discomfort to the patient, rejection and side effects due to frequent administration, and is also problematic because the person performing administration is limited to a person who has received medical education. In addition, the method of subcutaneous injection of the formulation in the form of a liquid has a disadvantage in that antibody content is 120 mg/mL, and thus the number of administrations and administration cycles may be limited.

Therefore, it is necessary for a stable liquid pharmaceutical formulation capable of including an antibody, particularly trastuzumab, as a HER2 inhibitor while solving the problems with conventional liquid pharmaceutical formulations.

DISCLOSURE

Technical Problem

An objective of the present invention is to provide a stable liquid pharmaceutical formulation having low viscosity not only when antibody content is low but also when antibody content is high.

Another objective of the present invention is to provide a liquid pharmaceutical formulation having superior long-term storage stability based on superior stability observed under accelerated conditions and harsh conditions.

Still another objective of the present invention is to provide a stable liquid pharmaceutical formulation that enables intravenous administration or subcutaneous administration.

Technical Solution

A stable liquid pharmaceutical formulation according to an embodiment of the present invention includes (A) an antibody or antigen-binding fragment thereof, (B) a surfactant, (C) a sugar or a sugar derivative, (D) a buffer, and (E) a stabilizer.

In an embodiment of the present invention, (A) the antibody may include an antibody that binds to HER2.

In an embodiment of the present invention, (A) the antibody may include trastuzumab, pertuzumab, or a mixture thereof.

In an embodiment of the present invention, (A) the antibody may include a humanized IgG monoclonal antibody.

In an embodiment of the present invention, (A) the antibody or antigen-binding fragment thereof may include a light-chain variable region including a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3, and a heavy-chain variable region including a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6.

In an embodiment of the present invention, (A) the antibody or antigen-binding fragment thereof may include a light-chain variable region comprising the amino acid sequence of SEQ ID NO: 7 and a heavy-chain variable region comprising the amino acid sequence of SEQ ID NO: 8.

In an embodiment of the present invention, (A) the antibody may include a light chain comprising the amino acid sequence of SEQ ID NO:9 and a heavy chain comprising the amino acid sequence of SEQ ID NO:10.

In an embodiment of the present invention, the concentration of (A) the antibody or antigen-binding fragment thereof may be 250 mg/ml or less.

In an embodiment of the present invention, (B) the surfactant may include polysorbate, poloxamer, or a mixture thereof.

In an embodiment of the present invention, (B) the surfactant may include Polysorbate 20, Polysorbate 40, Polysorbate 60, Polysorbate 80, or a mixture of two or more thereof.

In an embodiment of the present invention, (B) the surfactant may include Polysorbate 80.

In an embodiment of the present invention, the concentration of (B) the surfactant may be 0.02 to 0.1% (w/v).

In an embodiment of the present invention, (C) the sugar may include a monosaccharide, a disaccharide, an oligosaccharide, a polysaccharide, or a mixture of two or more thereof, and (C) the sugar derivative may include a sugar alcohol, a sugar acid, or a mixture thereof.

In an embodiment of the present invention, (C) the sugar or the sugar derivative may include sorbitol, mannitol, trehalose, sucrose, or a mixture of two or more thereof.

In an embodiment of the present invention, the concentration of (C) the sugar or the sugar derivative may be 1 to 10% (w/v).

In an embodiment of the present invention, (D) the buffer may include acetate.

In an embodiment of the present invention, the content of (D) the buffer may be 1 to 50 mM.

In an embodiment of the present invention, (E) the stabilizer may include methionine, aspartic acid, proline, or a mixture of two or more thereof.

In an embodiment of the present invention, (E) the stabilizer may include methionine.

In an embodiment of the present invention, the content of (E) the stabilizer may be 5 to 100 mM.

In an embodiment of the present invention, the pH may be 4.5 to 6.0.

In an embodiment of the present invention, NaCl, KCl, NaF, KBr, NaBr, $Na_2SO_4$, NaSCN, $K_2SO_4$, or a mixture thereof may not be included.

A stable liquid pharmaceutical formulation according to an embodiment of the present invention may include (A) an antibody or antigen-binding fragment thereof, including a light-chain variable region including a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3 and a heavy-chain variable region including a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6, (B) a surfactant, (C) a sugar or a sugar derivative, (D) a buffer including acetate, and (E) a stabilizer including methionine.

A stable liquid pharmaceutical formulation according to an embodiment of the present invention may include (A) 250 mg/ml or less of an antibody or antigen-binding fragment thereof, including a light-chain variable region including a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3 and a heavy-chain variable region including a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6, (B) 0.02 to 0.1% (w/v) of a surfactant, (C) 1 to 10% (w/v) of a sugar or a sugar derivative, (D) 1 to 50 mM of a buffer, and (E) 5 to 100 mM of a stabilizer.

In an embodiment of the present invention, the stable liquid pharmaceutical formulation may be used for intravenous administration or subcutaneous administration.

In an embodiment of the present invention, the stable liquid pharmaceutical formulation may not undergo either or both of a reconstitution step and a dilution step before use.

A pre-filled syringe according to an embodiment of the present invention may be filled with the stable liquid pharmaceutical formulation described above.

An auto-injector according to an embodiment of the present invention may include the pre-filled syringe therein.

Advantageous Effects

According to the present invention, a stable liquid pharmaceutical formulation has low viscosity not only when antibody content is low but also when antibody content is high, and exhibits superior long-term storage stability based on superior stability observed under accelerated conditions and harsh conditions.

MODE FOR INVENTION

[Stable Liquid Pharmaceutical Formulation]

A stable liquid pharmaceutical formulation according to the present invention includes (A) an antibody or antigen-binding fragment thereof, (B) a surfactant, (C) a sugar or a sugar derivative, (D) a buffer, and (E) a stabilizer.

As used herein, the expression "not comprise" or "not include" may mean that absolutely none of the corresponding component is contained. Also, the above expression may mean that the corresponding component is not substantially contained, that is, is contained within a range that does not affect the activity of the antibody or the stability and viscosity of the liquid pharmaceutical formulation, for example to the level of 0 to 1% (w/v), 0 to 1 ppm (w/v) or 0 to 1 ppb (w/v) based on the total weight of the liquid pharmaceutical formulation.

(A) Antibody or Antigen-Binding Fragment Thereof

The antibody is an immunoglobulin molecule comprising four polypeptide chains configured such that two heavy chains and two light chains are connected to each other by means of disulfide bonds. Naturally occurring antibodies having other changed structures, for example, camelid antibodies, are also included in the above definition. Each heavy chain is composed of a heavy-chain variable region and a heavy-chain constant region. The heavy-chain constant region is composed of three domains (CH1, CH2 and CH3). Each light chain is composed of a light-chain variable region and a light-chain constant region. The light-chain constant region is composed of one domain (CL). The heavy-chain variable region and the light-chain variable region may be further subdivided into a hypervariable region, called a complementarity-determining region (CDR), disposed together with a more conserved region, called a framework region (FR). Each of the heavy-chain variable region and the light-chain variable region is composed of three CDRs and four FRs, which are arranged in the following sequence from the amino terminal to the carboxyl terminal: FR1, CDR1, FR2, CDR2, FR3, CDR3, FR4.

In an embodiment of the present invention, the antibody may include a polyclonal antibody, a monoclonal antibody, a recombinant antibody, a single-chain antibody, a hybrid antibody, a chimeric antibody, a humanized antibody, or a fragment thereof. A humanized antibody refers to an antibody comprising heavy-chain and light-chain constant region sequences from any one species and variable region sequences from humans. In an embodiment of the present invention, the antibody may include a humanized IgG monoclonal antibody. The humanized IgG monoclonal antibody is composed of mouse heavy-chain and light-chain constant regions and human heavy-chain and light-chain variable regions bound thereto.

In an embodiment of the present invention, the antibody may include an antibody that binds to HER2 or an epitope of HER2. The antibody that binds to HER2 or an epitope of HER2 may include trastuzumab, pertuzumab, or a mixture thereof. In an embodiment of the present invention, the antibody may include trastuzumab.

In an embodiment of the present invention, the antibody may include a light-chain variable region including a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3, and a heavy-chain variable region including a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6.

In an embodiment of the present invention, the antibody may include a light-chain variable region comprising the amino acid sequence of SEQ ID NO:7 and a heavy-chain variable region comprising the amino acid sequence of SEQ ID NO:8.

In an embodiment of the present invention, the antibody may include a light chain comprising the amino acid sequence of SEQ ID NO:9 and a heavy chain comprising the amino acid sequence of SEQ ID NO:10.

The concentration of the antibody or antigen-binding fragment thereof may be freely adjusted within a range that does not substantially adversely affect the stability and viscosity of the stable liquid pharmaceutical formulation according to the present invention. In an embodiment of the present invention, the concentration of the antibody or antigen-binding fragment thereof may be 10 to 250 mg/ml. In another embodiment of the present invention, the concentration of the antibody or antigen-binding fragment thereof may be 10 to 250 mg/mL, 20 to 250 mg/mL, 30 to 250 mg/mL, 40 to 250 mg/mL, 50 to 250 mg/mL, 60 to 250 mg/mL, 70 to 250 mg/mL, 80 to 250 mg/mL, 90 to 250 mg/mL, 100 to 250 mg/mL, 110 to 250 mg/mL, 120 to 250 mg/mL, 130 to 250 mg/mL, 140 to 250 mg/mL, 150 to 250 mg/mL, 160 to 250 mg/mL, 170 to 250 mg/mL, 180 to 250 mg/mL, 190 to 250 mg/mL, 200 to 250 mg/mL, 210 to 250 mg/mL, or 220 to 250 mg/mL. In still another embodiment of the present invention, the concentration of the antibody or antigen-binding fragment thereof may be 10 to 240 mg/mL, 10 to 230 mg/mL, 10 to 220 mg/mL, 10 to 210 mg/mL, 10 to 200 mg/mL, 10 to 190 mg/mL, 10 to 180 mg/mL, 10 to 170 mg/mL, 10 to 160 mg/mL, 10 to 150 mg/mL, 10 to 140 mg/mL, 10 to 130 mg/mL, 10 to 120 mg/mL, 10 to 110 mg/mL, 10 to 100 mg/mL, 10 to 90 mg/mL, 10 to 80 mg/mL, 10 to 70 mg/mL, 10 to 60 mg/mL, 10 to 50 mg/mL, 10 To 40 mg/mL, 10 to 30 mg/mL, or 10 to 20 mg/mL. When the concentration of the antibody or antigen-binding fragment thereof falls within the above range, freedom to determine the dose and frequency of administration may increase due to the high content of the antibody or antigen-binding fragment thereof, and superior long-term stability and low viscosity may be exhibited.

(B) Surfactant

Examples of the surfactant may include, but are not limited to, polyoxyethylene sorbitan fatty acid ester (e.g. Polysorbate), polyoxyethylene alkyl ether (e.g. Brij), alkylphenyl polyoxyethylene ether (e.g. Triton-X), a polyoxyethylene-polyoxypropylene copolymer (e.g. Poloxamer, Pluronic), sodium dodecyl sulfate (SDS), and the like.

In an embodiment of the present invention, the surfactant may include polyoxyethylene sorbitan fatty acid ester (Polysorbate). The Polysorbate may include Polysorbate 20, Polysorbate 40, Polysorbate 60, Polysorbate 80, or a mixture of two or more thereof. In an embodiment of the present invention, the Polysorbate may include Polysorbate 20, Polysorbate 80, or a mixture thereof. In another embodiment of the present invention, the Polysorbate may include Polysorbate 80.

In an embodiment of the present invention, the concentration of the surfactant may be freely adjusted within a range that does not adversely affect the stability and viscosity of the stable liquid pharmaceutical formulation according to the present invention. For example, the concentration of the surfactant may be 0.001 to 5% (w/v), 0.01 to 1% (w/v), or 0.02 to 0.1% (w/v). When the concentration of the surfactant falls within the above range, superior long-term stability and low viscosity may be exhibited.

(C) Sugar or Sugar Derivative

The sugar may include a monosaccharide, a disaccharide, an oligosaccharide, a polysaccharide, or a mixture of two or more thereof. Examples of the monosaccharide may include, but are not limited to, glucose, fructose, galactose, and the like. Examples of the disaccharide may include, but are not limited to, sucrose, lactose, maltose, trehalose, and the like. Examples of the oligosaccharide may include, but are not limited to, fructo-oligosaccharide, galacto-oligosaccharide, mannan-oligosaccharide, and the like. Examples of the polysaccharide may include, but are not limited to, starch, glycogen, cellulose, chitin, pectin, and the like.

The sugar derivative may include a sugar alcohol, a sugar acid, or a mixture thereof. Examples of the sugar alcohol may include, but are not limited to, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, and the like. Examples of the sugar acid may include, but are not limited to, aldonic acid (glyceric acid, etc.), ulosonic acid (neuraminic acid, etc.), uronic acid (glucuronic acid, etc.), aldaric acid (tartaric acid, etc.), and the like.

In an embodiment of the present invention, the sugar or the sugar derivative may include sorbitol, mannitol, trehalose, sucrose, or a mixture of two or more thereof.

In an embodiment of the present invention, the concentration of the sugar or the sugar derivative may be freely adjusted within a range that does not substantially adversely affect the stability and viscosity of the liquid pharmaceutical formulation according to the present invention. For example, the concentration of the sugar or the sugar derivative may be 0.1 to 30% (w/v), 1 to 20% (w/v), or 1 to 10% (w/v). When the concentration of the sugar or the sugar derivative falls within the above range, superior long-term stability and low viscosity may be exhibited.

(D) Buffer

The buffer is a neutralizing substance that minimizes a change in pH caused by an acid or an alkali Examples of the buffer may include phosphate, acetate, succinate, gluconate, glutamate, citrate, histidine, and the like.

In an embodiment of the present invention, the acetate buffer may include acetate. Examples of the acetate may include, but are not limited to, sodium acetate, zinc acetate, aluminum acetate, ammonium acetate, potassium acetate, and the like. The acetate buffer may be prepared by mixing the acetate with acetic acid. In an embodiment of the present invention, an acetate buffer solution may include sodium acetate.

In an embodiment of the present invention, the stable liquid pharmaceutical formulation may not include histidine, citrate (citric acid salt), phosphate (phosphoric acid salt), or a mixture thereof.

In an embodiment of the present invention, the acetate content in the acetate buffer may be freely adjusted within a range that does not substantially adversely affect the stability and viscosity of the liquid pharmaceutical formulation according to the present invention. For example, the content of the acetate buffer may be 1 to 50 mM, 5 to 30 mM, or 10 to 25 mM. When the acetate content falls within the above range, superior long-term stability and low viscosity may be exhibited.

Meanwhile, the acetate content is the content of acetate in the formulation stored in a single container, and in the case of a container intended for distribution or multiple administrations, the acetate content may increase several times depending on the number of distributions or the number of administrations. On the other hand, in the case of a small container, the acetate content may be reduced corresponding thereto.

(E) Stabilizer

In an embodiment of the present invention, the stable liquid pharmaceutical formulation may include, as a stabilizer, methionine, aspartic acid, proline, or a mixture of two or more thereof. Also, in an embodiment of the present invention, the stabilizer may include methionine. For example, amino acid as the stabilizer may be included in the content range of 3 to 100 mM, for example, 5 to 100 mM, 5 to 50 mM, 5 to 30 mM, or 5 to 15 mM. When the content of the stabilizer falls within the above range, high-molecular-weight component content or low-molecular-weight component content may be maintained low for a long period of time, intact immunoglobulin G component content or intact heavy-chain and light-chain content may be maintained high, and superior long-term stability and low viscosity may be exhibited.

(F) pH

The pH of the stable liquid pharmaceutical composition according to the present invention may be freely adjusted within a range that does not substantially adversely affect the stability and viscosity of the liquid pharmaceutical formulation according to the present invention. For example, the pH of the present composition may be 4.5 to 6.0, 5.0 to 6.0, or 5.0 to 5.5. When the pH thereof falls within the above range, superior long-term stability and low viscosity may be exhibited. The pH may be adjusted using an acetate buffer solution. Specifically, when the acetate buffer solution is included in a predetermined content, the pH in the above range may be realized even without the use of a separate pH controller. When using a buffer solution including histidine, citrate, phosphate, or a mixture thereof, it may be difficult to achieve the pH in the above range. When an acid or a base (e.g. sodium hydroxide) is additionally included as a separate pH controller, the stability of the antibody may be deteriorated.

(G) Other Components

In an embodiment of the present invention, the stable liquid pharmaceutical formulation may not include salts. When salts are included, a precipitation phenomenon may occur, and the resulting formulation may have a gelatin-like appearance and poor stability. Examples of the salts may include, but are not limited to, NaCl, KCl, NaF, KBr, NaBr, $Na_2SO_4$, NaSCN, $K_2SO_4$, and the like.

In an embodiment of the present invention, the stable liquid pharmaceutical formulation may not include a preservative. Examples of the preservative may include octadecyl dimethylbenzyl ammonium chloride, hexamethonium chloride, benzalkonium chloride, benzethonium chloride, phenol, butyl alcohol, benzyl alcohol, alkyl paraben, catechol, resorcinol, cyclohexanol, 3-pentanol, m-cresol, and the like. When such a preservative is included, it may not help to improve stability.

In an embodiment of the present invention, the stable liquid pharmaceutical formulation of the present invention may further include an additive known in the art within a range that does not substantially adversely affect the activity of the antibody or the stability and low viscosity of the formulation. For example, an aqueous carrier, an antioxidant, or a mixture of two or more thereof may be further included. The aqueous carrier is a carrier that is pharmaceutically acceptable (safe and nontoxic upon administration to humans) and is useful for the preparation of a liquid pharmaceutical formulation. Examples of the aqueous carrier may include, but are not limited to, sterile water for injection (SWFI), bacteriostatic water for injection (BWFI), a sterile saline solution, Ringer's solution, dextrose, and the like. Examples of the antioxidant may include, but are not limited to, ascorbic acid and the like.

(H) "Stable" Liquid Pharmaceutical Formulation

The term "stable" in the stable liquid pharmaceutical formulation of the present invention may mean that the antibody according to the invention substantially retains its physical stability, chemical stability, and/or biological activity during the preparation process and/or upon storage. A variety of analytical techniques for measuring the stability of antibodies are readily available in the art.

Physical stability may be assessed by methods known in the art, including measuring the apparent attenuation of light (absorbance or optical density) by the sample. This light attenuation measurement is related to the turbidity of the formulation. Also, for physical stability, high-molecular-weight component content, main component content, low-molecular-weight component content, intact immunoglobulin G content, intact heavy-chain and light-chain content, the number of subvisible particles and the like may be measured.

Chemical stability may be assessed, for example, by detecting and quantifying the antibody in a chemically altered form. Chemical stability includes charge changes (e.g. occurring as a result of deamidation or oxidation), which may be assessed, for example, by ion exchange chromatography. For chemical stability, charge variants (acidic or basic peaks) and the like may be measured.

Biological activity may be assessed by methods known in the art, and antigen-binding affinity may be measured through, for example, ELISA.

In an embodiment of the present invention, the liquid pharmaceutical formulation may be stable for a long period of time.

In an embodiment of the present invention, the term "stable" liquid pharmaceutical formulation refers to a liquid pharmaceutical formulation satisfying at least one of the following.

Turbidity

A liquid pharmaceutical formulation having an absorbance A600 of 0 to 0.0110 as measured using a spectrophotometer after storage for 7 weeks at a temperature of 40° C.±2° C.

A liquid pharmaceutical formulation having an absorbance A600 of 0 to 0.0110 as measured using a spectrophotometer after storage for 7 weeks at a temperature of 40° C.±2° C. and a relative humidity of 75±5% under airtight conditions Main Component Content (Main Peak)

A liquid pharmaceutical formulation including 99 to 100% of a main component, as measured by SE-HPLC after storage for 7 weeks at a temperature of 5° C.±3° C.

A liquid pharmaceutical formulation including 99 to 100% of a main component, as measured by SE-HPLC after storage for 7 weeks at a temperature of 5° C.±3° C. under airtight conditions A liquid pharmaceutical formulation including 98% to 100% of a main component, as measured by SE-HPLC after storage for 6 weeks at a temperature of 25° C.±2° C.

A liquid pharmaceutical formulation including 98 to 100% of a main component, as measured by SE-HPLC after storage for 6 weeks at a temperature of 25° C.±2° C. and a relative humidity of 60±5% under airtight conditions A liquid pharmaceutical formulation including 97% to 100% of a main component, as measured by SE-HPLC after storage for 7 weeks at a temperature of 40° C.±2° C.

A liquid pharmaceutical formulation including 97 to 100% of a main component, as measured by SE-HPLC after storage for 7 weeks at a temperature of 40° C.±2° C. and a relative humidity of 75±5% under airtight conditions High-Molecular-Weight Component (a Peak in which the Retention Time Thereof is Located Before a Main Peak (Intact IgG))

A liquid pharmaceutical formulation including 0 to 1.0% of a high-molecular-weight component, as measured by SE-HPLC after storage for 7 weeks at a temperature of 5° C.±3° C.

A liquid pharmaceutical formulation including 0 to 1.0% of a high-molecular-weight component, as measured by SE-HPLC after storage for 7 weeks at a temperature of 5° C.±3° C. under airtight conditions A liquid pharmaceutical formulation including 0 to 1.0% of a high-molecular-weight component, as measured by SE-HPLC after storage for 6 weeks at a temperature of 25° C.±2° C.

A liquid pharmaceutical formulation including 0 to 1.0% of a high-molecular-weight component, as measured by SE-HPLC after storage for 6 weeks at a temperature of 25° C.±2° C. and a relative humidity of 60±5% under airtight conditions A liquid pharmaceutical formulation including 0% to 2.5% of a high-molecular-weight component, as measured by SE-HPLC after storage for 7 weeks at a temperature of 40° C.±2° C.

A liquid pharmaceutical formulation including 0 to 2.5% of a high-molecular-weight component, as measured by SE-HPLC after storage for 7 weeks at a temperature of 40° C.±2° C. and a relative humidity of 75±5% under airtight conditions Low-Molecular-Weight Component (a Peak in which the Retention Time Thereof is Located after a Main Peak (Intact IgG))

A liquid pharmaceutical formulation including 0 to 0.2% of a low-molecular-weight component, as measured by SE-HPLC after storage for 7 weeks at a temperature of 5° C.±3° C.

A liquid pharmaceutical formulation including 0 to 0.2% of a low-molecular-weight component, as measured by SE-HPLC after storage for 7 weeks at a temperature of 5° C.±3° C. under airtight conditions A liquid pharmaceutical formulation including 0 to 0.3% of a low-molecular-weight component, as measured by SE-HPLC after storage for 6 weeks at a temperature of 25° C.±2° C.

A liquid pharmaceutical formulation including 0 to 0.3% of a low-molecular-weight component, as measured by SE-HPLC after storage for 6 weeks at a temperature of 25° C.±2° C. and a relative humidity of 60±5% under airtight conditions A liquid pharmaceutical formulation including 0% to 2.0% of a low-molecular-weight component, as measured by SE-HPLC after storage for 7 weeks at a temperature of 40° C.±2° C.

A liquid pharmaceutical formulation including 0 to 2.0% of a low-molecular-weight component, as measured by SE-HPLC after storage for 7 weeks at a temperature of 40° C.±2° C. and a relative humidity of 75±5% under airtight conditions Intact Immunoglobulin G Content A liquid pharmaceutical formulation having an intact immunoglobulin G content (intact IgG %) of 97.0% to 100%, as measured by non-reduced CE-SDS after storage for 7 weeks at a temperature of 5° C.±3° C.

A liquid pharmaceutical formulation having an intact immunoglobulin G content (intact IgG %) of 97.0% to 100%, as measured by non-reduced CE-SDS after storage for 7 weeks at a temperature of 5° C.±3° C. under airtight conditions A liquid pharmaceutical formulation having an intact immunoglobulin G content (intact IgG %) of 96.0% to 100%, as measured by non-reduced CE-SDS after storage for 6 weeks at a temperature of 25° C.±2° C.

A liquid pharmaceutical formulation having an intact immunoglobulin G content (intact IgG %) of 96.0% to 100%, as measured by non-reduced CE-SDS after storage for 6 weeks at a temperature 25° C.±2° C. and a relative humidity of 60±5% under airtight conditions A liquid pharmaceutical formulation having an intact immunoglobulin G content (intact IgG %) of 90.4% to 100%, as measured by non-reduced CE-SDS after storage for 7 weeks at a temperature of 40° C.±2° C.

A liquid pharmaceutical formulation having an intact immunoglobulin G content (intact IgG %) of 90.4% to 100%, as measured by non-reduced CE-SDS after storage for 7 weeks at a temperature of 40° C.±2° C. and a relative humidity of 75±5% under airtight conditions Intact Heavy-Chain and Light-Chain Content A liquid pharmaceutical formulation having an intact heavy-chain and light-chain content (intact HC+LC %) of 99.0% to 100%, as measured by reduced CE-SDS after storage for 7 weeks at a temperature of 5° C.±3° C.

A liquid pharmaceutical formulation having an intact heavy-chain and light-chain content (intact HC+LC %) of 99.0% to 100%, as measured by reduced CE-SDS after storage for 7 weeks at a temperature of 5° C.±3° C. under airtight conditions A liquid pharmaceutical formulation having an intact heavy-chain and light-chain content (intact HC+LC %) of 99.1% to 100%, as measured by reduced CE-SDS after storage for 6 weeks at a temperature of 25° C.±2° C.

A liquid pharmaceutical formulation having an intact heavy-chain and light-chain content (intact HC+LC %) of 99.1% to 100%, as measured by reduced CE-SDS after storage for 6 weeks at a temperature of 25° C.±2° C. and a relative humidity of 60±5% under airtight conditions A liquid pharmaceutical formulation having an intact heavy-chain and light-chain content (intact HC+LC %) of 96.8% to 100%, as measured by reduced CE-SDS after storage for 7 weeks at a temperature of 40° C.±2° C.

A liquid pharmaceutical formulation having an intact heavy-chain and light-chain content (intact HC+LC %) of 96.8% to 100%, as measured by reduced CE-SDS after storage for 7 weeks at a temperature of 40° C.±2° C. and a relative humidity of 75±5% under airtight conditions Number of Subvisible Particles A liquid pharmaceutical formulation in which the number of subvisible particles (10.00 µm≤, <100.00 µm) is 0 to 100, as measured by MFI after storage for 7 weeks at a temperature of 5° C.±3° C.

A liquid pharmaceutical formulation in which the number of subvisible particles (10.00 µm≤, <100.00 µm) is 0 to 100, as measured by MFI after storage for 7 weeks at a temperature of 5° C.±3° C. under airtight conditions A liquid pharmaceutical formulation in which the number of subvisible particles (1.00 µm≤, <100.00 µm) is 0 to 3000, as measured by MRI after storage for 7 weeks at a temperature of 5° C.±3° C.

A liquid pharmaceutical formulation in which the number of subvisible particles (1.00 µm≤, <100.00 µm) is 0 to 3000, as measured by MRI after storage for 7 weeks at a temperature of 5° C.±3° C. under airtight conditions A liquid pharmaceutical formulation in which the number of subvisible particles (10.00 µm≤, <100.00 µm) is 0 to 100, as measured by MFI after storage for 6 weeks at a temperature of 25° C.±2° C.

A liquid pharmaceutical formulation in which the number of subvisible particles (10.00 µm≤, <100.00 µm) is 0 to 100, as measured by MFI after storage for 6 weeks at a temperature of 25° C.±2° C. and a relative humidity of 60±5% under airtight conditions A liquid pharmaceutical formulation in which the number of subvisible particles (1.00 µm≤, <100.00 µm) is 0 to 4,000, as measured by MFI after storage for 6 weeks at 25° C.±2° C.

A liquid pharmaceutical formulation in which the number of subvisible particles (1.00 µm≤, <100.00 µm) is 0 to 4,000, as measured by MFI after storage for 6 weeks at 25° C.±2° C. and a relative humidity of 60±5% under airtight conditions A liquid pharmaceutical formulation in which the number of subvisible particles (10.00 µm≤, <100.00 µm) is 0 to 200, as measured by MFI after storage for 7 weeks at a temperature of 40° C.±2° C.

A liquid pharmaceutical formulation in which the number of subvisible particles (10.00 µm≤, <100.00 µm) is 0 to 200, as measured by MFI after storage for 7 weeks at a temperature of 40° C.±2° C. and a relative humidity of 75±5% under airtight conditions A liquid pharmaceutical formulation in which the number of subvisible particles (1.00 µm≤, <100.00 µm) is 0 to 7,000, as measured by MFI after storage for 7 weeks at a temperature of 40° C.±2° C.

A liquid pharmaceutical formulation in which the number of subvisible particles (1.00 µm≤, <100.00 µm) is 0 to 7,000, as measured by MFI after storage for 7 weeks at a temperature of 40° C.±2° C. and a relative humidity of 75±5% under airtight conditions Oxidation Rate A liquid pharmaceutical formulation in which the oxidation rate of heavy-chain Met 255 is 0% to 3.0%, as measured by LC-MS after storage for 7 weeks at a temperature of 5° C.±3° C.

A liquid pharmaceutical formulation in which the oxidation rate of heavy-chain Met 255 is 0% to 3.0%, as measured by LC-MS after storage for 7 weeks at a temperature of 5° C.±3° C. under airtight conditions A liquid pharmaceutical formulation in which the oxidation rate of heavy-chain Met 255 is 0% to 2.1%, as measured by LC-MS after storage for 6 weeks at a temperature of 25° C.±2° C.

A liquid pharmaceutical formulation in which the oxidation rate of heavy-chain Met 255 is 0% to 2.1%, as measured by LC-MS after storage for 6 weeks at a temperature of 25° C.±2° C. and a relative humidity of 60±5% under airtight conditions A liquid pharmaceutical formulation in which the oxidation rate of heavy-chain Met 255 is 0% to 5.7%, as measured by LC-MS after storage for 7 weeks at a temperature of 40° C.±2° C.

A liquid pharmaceutical formulation in which the oxidation rate of heavy-chain Met 255 is 0% to 5.7%, as measured by LC-MS after storage for 7 weeks at a temperature of 40° C.±2° C. and a relative humidity of 75±5% under airtight conditions Charge Variant A liquid pharmaceutical formulation in which the acidic peak is 20% to 32%, as measured by IEC-HPLC after storage for 7 weeks at a temperature of 5° C.±3° C.

A liquid pharmaceutical formulation in which the acidic peak is 20% to 32%, as measured by IEC-HPLC after storage for 7 weeks at a temperature of 5° C.±3° C. under airtight conditions A liquid pharmaceutical formulation in which the acidic peak is 22% to 30%, as measured by IEC-HPLC after storage for 6 weeks at a temperature of 25° C.±2° C.

A liquid pharmaceutical formulation in which the acidic peak is 22% to 30%, as measured by IEC-HPLC after storage for 6 weeks at a temperature of 25° C.±2° C. and a relative humidity of 60±5% under airtight conditions A liquid pharmaceutical formulation in which the acidic peak is 19% to 34%, as measured by IEC-HPLC after storage for 7 weeks at a temperature of 40° C.±2° C.

A liquid pharmaceutical formulation in which the acidic peak is 19% to 34%, as measured by IEC-HPLC after storage for 7 weeks at a temperature of 40° C.±2° C. and a relative humidity of 75±5% under airtight conditions A liquid pharmaceutical formulation in which the main peak is 50% to 60%, as measured by IEC-HPLC after storage for 7 weeks at a temperature of 5° C.±3° C.

A liquid pharmaceutical formulation in which the main peak is 50% to 60%, as measured by IEC-HPLC after storage for 7 weeks at a temperature of 5° C.±3° C. under airtight conditions A liquid pharmaceutical formulation in which the main peak is 40% to 48%, as measured by IEC-HPLC after storage for 6 weeks at a temperature of 25° C.±2° C.

A liquid pharmaceutical formulation in which the main peak is 40% to 48%, as measured by IEC-HPLC after storage for 6 weeks at a temperature of 25° C.±2° C. and a relative humidity of 60±5% under airtight conditions A liquid pharmaceutical formulation in which the main peak is 19% to 30%, as measured by IEC-HPLC after storage for 7 weeks at a temperature of 40° C.±2° C.

A liquid pharmaceutical formulation in which the main peak is 19% to 30%, as measured by IEC-HPLC after storage for 7 weeks at a temperature of 40° C.±2° C. and a relative humidity of 75±5% under airtight conditions A liquid pharmaceutical formulation in which the basic peak is 12% to 20%, as measured by IEC-HPLC after storage for 7 weeks at a temperature of 5° C.±3° C.

A liquid pharmaceutical formulation in which the basic main peak is 12% to 20%, as measured by IEC-HPLC after storage for 7 weeks at a temperature of 5° C.±3° C. under airtight conditions A liquid pharmaceutical formulation in which the basic peak is 26% to 37%, as measured by IEC-HPLC after storage for 6 weeks at a temperature of 25° C.±2° C.

A liquid pharmaceutical formulation in which the basic main peak is 26% to 37%, as measured by IEC-HPLC after storage for 6 weeks at a temperature of 25° C.±2° C. and a relative humidity of 60±5% under airtight conditions A liquid pharmaceutical formulation in which the basic peak is 40% to 66%, as measured by IEC-HPLC after storage for 7 weeks at a temperature of 40° C.±2° C.

A liquid pharmaceutical formulation in which the basic peak is 40% to 66%, as measured by IEC-HPLC after storage for 7 weeks at a temperature of 40° C.±2° C. and a relative humidity of 75±5% under airtight conditions HER2-Binding Affinity A liquid pharmaceutical formulation having a HER2-binding affinity of 80% to 120%, as measured by ELISA after storage for 7 weeks at a temperature of 5° C.±3° C.

A liquid pharmaceutical formulation having a HER2-binding affinity of 80% to 120%, as measured by ELISA after storage for 7 weeks at a temperature of 5° C.±3° C. under airtight conditions A liquid pharmaceutical formulation having a HER2-binding affinity of 80% to 120%, as measured by ELISA after storage for 6 weeks at a temperature of 25° C.±2° C.

A liquid pharmaceutical formulation having a HER2-binding affinity of 80% to 120%, as measured by ELISA after storage for 6 weeks at a temperature of 25° C.±2° C. and a relative humidity of 60±5% under airtight conditions A liquid pharmaceutical formulation having a HER2-binding affinity of 80% to 120%, as measured by ELISA after storage for 7 weeks at a temperature of 40° C.±2° C.

A liquid pharmaceutical formulation having a HER2-binding affinity of 80% to 120%, as measured by ELISA after storage for 7 weeks at a temperature of 40° C.±2° C. and a relative humidity of 75±5% under airtight conditions

[Method of Preparing Stable Liquid Pharmaceutical Formulation]

The stable liquid pharmaceutical formulation according to the present invention may be prepared using any known method, and the preparation thereof is not limited to any specific method. For example, a liquid pharmaceutical formulation may be prepared by adjusting the pH of a solution including a surfactant and a sugar or derivative thereof through the addition of an acetate buffer solution, and then adding the resulting mixed solution with an antibody.

Also, upon preparation of the liquid pharmaceutical formulation, a freeze-drying process may or may not be performed.

When a freeze-drying process is not performed, for example, the liquid pharmaceutical formulation of the present invention is prepared and may be placed in an airtight container immediately after treatment such as sterile treatment or the like.

When a freeze-drying process is performed, for example, the liquid pharmaceutical formulation of the present invention may be prepared and freeze-dried, or the liquid pharmaceutical formulation of the present invention may be prepared, freeze-dried and stored, followed by replenishing or replacing any component removed or modified through freeze-drying and/or storage, thereby obtaining the liquid pharmaceutical formulation of the present invention. Also, only components other than components that may be removed or modified through freeze-drying and/or storage in the liquid pharmaceutical formulation of the present invention may be freeze-dried, or may be freeze-dried and stored, after which those components may be added thereto, thereby obtaining the liquid pharmaceutical formulation of the present invention.

[Method of Using Stable Liquid Pharmaceutical Formulation]

The stable liquid pharmaceutical formulation according to the present invention may be used to treat harmful diseases through HER2 binding. Examples of diseases to which the activity of HER2 is detrimental may include, but are not limited to, breast cancer, rectal cancer, gastrointestinal cancer, and the like.

In an embodiment of the present invention, harmful diseases due to binding to HER2 may be selected from among breast cancer, rectal cancer, and gastrointestinal cancer. The stable liquid pharmaceutical formulation according to the present invention may be used once or several times, or may be used for intravenous administration or subcutaneous administration.

The concentrations of the antibody and other components in the liquid pharmaceutical formulation are as described above, and the total volume of the liquid pharmaceutical formulation may be 0.2 to 3.5 mL.

The dose and timing of administration of the liquid pharmaceutical formulation may vary depending on the type of disease, the severity and course of the disease, the patient's health and treatment regime, and the judgment of the attending doctor, and are not limited to specific values. For example, a single product or several products containing the liquid pharmaceutical formulation may be administered in a dose of 600 mg based on the concentration of the antibody, after which administration in the same dose may be performed every 3 weeks.

[Treatment Method and Stabilization Method]

The present invention also provides a method of treating a disease to which the activity of HER2 is detrimental, including administering, to a patient suffering from a disease to which the activity of HER2 is detrimental, a stable liquid pharmaceutical formulation including (A) an antibody or antigen-binding fragment thereof, (B) a surfactant, (C) a sugar or a sugar derivative, (D) a buffer, and (E) a stabilizer.

In addition, the present invention provides a method of stabilizing a stable liquid pharmaceutical formulation, including (A) an antibody or antigen-binding fragment thereof, (B) a surfactant, (C) a sugar or a sugar derivative, (D) a buffer, and (E) a stabilizer, in a liquid pharmaceutical formulation.

In an embodiment of the treatment method or the stabilization method, the antibody may include an antibody that binds to HER2.

In one embodiment of the treatment method or the stabilization method, the antibody may include trastuzumab, pertuzumab, or a mixture thereof.

In an embodiment of the treatment method or the stabilization method, the antibody may include a humanized IgG monoclonal antibody.

In an embodiment of the treatment method or the stabilization method, the antibody may include a light-chain variable region including a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3 and a heavy-chain variable region including a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6.

In an embodiment of the treatment method or the stabilization method, the antibody may include a light-chain variable region comprising the amino acid sequence of SEQ ID NO:7 and a heavy-chain variable region comprising the amino acid sequence of SEQ ID NO:8.

In an embodiment of the treatment method or the stabilization method, the antibody may include a light chain comprising the amino acid sequence of SEQ ID NO:9 and a heavy chain comprising the amino acid sequence of SEQ ID NO:10.

In an embodiment of the treatment method or the stabilization method, the concentration of (A) the antibody or antigen-binding fragment thereof may be 250 mg/ml or less.

In an embodiment of the treatment method or the stabilization method, (B) the surfactant may include polysorbate, poloxamer, or a mixture thereof.

In an embodiment of the treatment method or the stabilization method, (B) the surfactant may include Polysorbate 20, Polysorbate 40, Polysorbate 60, Polysorbate 80, or a mixture of two or more thereof.

In an embodiment of the treatment method or the stabilization method, (B) the surfactant may include Polysorbate 80.

In an embodiment of the treatment method or the stabilization method, the concentration of (B) the surfactant may be 0.02 to 0.1% (w/v).

In an embodiment of the treatment method or the stabilization method, (C) the sugar may include a monosaccharide, a disaccharide, an oligosaccharide, a polysaccharide, or a mixture of two or more thereof, and the sugar derivative may include a sugar alcohol, a sugar acid, or a mixture thereof.

In an embodiment of the treatment method or the stabilization method, (C) the sugar or the sugar derivative may include sorbitol, mannitol, trehalose, sucrose, or a mixture of two or more thereof.

In an embodiment of the treatment method or the stabilization method, the concentration of (C) the sugar or the sugar derivative may be 1 to 10% (w/v).

In an embodiment of the treatment method or the stabilization method, (D) the buffer may include acetate.

In an embodiment of the treatment method or the stabilization method, the content of (D) the buffer may be 1 to 50 mM.

In an embodiment of the treatment method or the stabilization method, the stable liquid pharmaceutical formulation may include, as (E) the stabilizer, methionine, aspartic acid, proline, or a mixture of two or more thereof.

In an embodiment of the treatment method or the stabilization method, (E) the stabilizer may include methionine.

In an embodiment of the treatment method or the stabilization method, the content of (E) the stabilizer may be 5 to 100 mM.

In an embodiment of the treatment method or the stabilization method, the stable liquid pharmaceutical formulation may have a pH of 4.5 to 6.0.

In an embodiment of the treatment method or the stabilization method, the stable liquid pharmaceutical formulation may not include salts. In the case in which salts are included, a precipitation phenomenon may occur, and the resulting formulation may have a gelatin-like appearance. Examples of the salts may include, but are not limited to, NaCl, KCl, NaF, KBr, NaBr, $Na_2SO_4$, NaSCN, $K_2SO_4$, and the like.

In an embodiment of the treatment method or the stabilization method, the stable liquid pharmaceutical formulation may not include a preservative.

In an embodiment of the treatment method or the stabilization method, the stable liquid pharmaceutical formulation may further include an aqueous carrier, an antioxidant, or a mixture of two or more thereof.

In an embodiment of the treatment method or the stabilization method, there is provided a method of treating a disease to which the activity of HER2 is detrimental, including administering the stable liquid pharmaceutical formulation including (A) 250 mg/ml or less of an antibody or antigen-binding fragment thereof including a light-chain variable region including a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3 and a heavy-chain variable region including a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6, (B) 0.02 to 0.1% (w/v) of a surfactant, (C) 1 to 10% (w/v) of a sugar or a sugar derivative, (D) 1 to 50 mM of a buffer, and (E) 5 to 100 mM of a stabilizer.

In an embodiment of the treatment method or the stabilization method, the stable liquid pharmaceutical formulation may be used for intravenous administration or subcutaneous administration.

In an embodiment of the treatment method or the stabilization method, the stable liquid pharmaceutical formulation may have viscosity of less than 20 cP, as measured after preparation of a sample.

In an embodiment of the treatment method or the stabilization method, the stable liquid pharmaceutical formulation may not undergo either or both of a reconstitution step and a dilution step before use.

Also, in an embodiment of the treatment method or the stabilization method, the stable liquid pharmaceutical formulation may be loaded in a pre-filled syringe.

Also, in an embodiment of the treatment method or the stabilization method, the pre-filled syringe may be included in an auto-injector.

[Product]

The present invention also provides a product including the stable liquid pharmaceutical formulation and a container that accommodates the stable liquid pharmaceutical formulation in an airtight state.

The stable liquid pharmaceutical formulation is as described above.

In an embodiment of the present invention, the container may be formed of a material such as glass, a polymer (plastic), a metal, or the like, but is not limited thereto. In an embodiment of the present invention, the container is a bottle, a vial, a cartridge, an injector (a pre-filled syringe or an auto-injector), or a tube, but is not limited thereto. In an embodiment of the present invention, the container may be a vial made of glass or a polymer, or a pre-filled syringe made of glass or a polymer.

Specific product types of the vial, cartridge, pre-filled syringe, auto-injector, etc., and the method of filling the vial, cartridge, pre-filled syringe, auto-injector, etc. with the stable liquid pharmaceutical formulation may be easily obtained or implemented by those of ordinary skill in the art to which the present invention pertains. For example, U.S. Pat. Nos. 4,861,335, 6,331,174 and the like disclose specific product types and filling methods of pre-filled syringes. For example, U.S. Pat. Nos. 5,085,642, 5,681,291 and the like disclose specific product types and assembly methods of auto-injectors. As the vial, cartridge, pre-filled syringe, auto-injector, etc., a commercially available product may be used without change, or a separately custom-made product may be used in consideration of the physical properties, administration site, and dose of the stable liquid pharmaceutical formulation.

In an embodiment of the present invention, the inner surface of the container may not be coated with silicone oil. If coated with silicone oil, stability may be deteriorated. The container may be a single-dose or multi-dose container.

In an embodiment of the present invention, the product may further include instructions for either or both of the method of using the stable liquid pharmaceutical formulation and the method of storing the stable liquid pharmaceutical formulation. The usage method includes a cure for a disease to which the activity of HER2 is detrimental, and may include an administration route, dose, and timing.

In an embodiment of the present invention, the product may include other tools necessary from the viewpoint of a commercial purpose and a user, for example, a needle, an injector, and the like.

A better understanding of the present invention may be obtained through the following examples. These examples are merely set forth to illustrate the present invention and are not to be construed as limiting the scope of the present invention.

EXAMPLES

With regard to the antibodies used in the experimental examples below, trastuzumab, made by Celltrion, was used.

In order to measure the physical stability, chemical stability, and biological activity of the liquid pharmaceutical formulations used in the examples below, the following methods were used.

Turbidity

Absorbance was measured at 600 nm using a UV-Vis spectrophotometer.

High-Molecular-Weight Component Content

The high-molecular-weight component content (pre-peak; %) was measured using SE-HPLC (size exclusion high-performance liquid chromatography).

Main Component Content

The main component content (main peak; %) was measured using SE-HPLC.

Low-Molecular-Weight Component Content

The low-molecular-weight component content (post-peak; %) was measured using SE-HPLC.

Intact Immunoglobulin G Content (Intact IgG %)

The intact immunoglobulin G content (%) was measured using non-reduced CE-SDS (capillary electrophoresis-sodium dodecyl sulfate).

Intact Heavy-Chain and Light-Chain Content (Intact HC+LC %)

The intact heavy-chain and light-chain content (%) was measured using reduced CE-SDS (capillary electrophoresis-sodium dodecyl sulfate).

Number of Subvisible Particles

The number of subvisible particles was measured using MFI (micro flow imaging).

Oxidation Rate

The oxidation rate (%) of heavy-chain Met 255 was measured through peptide mapping using LC-MS (liquid chromatography—mass spectrometry).

Charge Variant

The acidic and main peaks (%) were measured using IEC-HPLC (ion exchange chromatography—high-performance liquid chromatography).

HER2-Binding Affinity

HER2-binding affinity (%) was measured using ELISA (enzyme-linked immunosorbent assay).

Viscosity

The viscosity in a 500 μL syringe was measured at 25° C.±0.1° C. using a micro-capillary rheometer (apparent shear rate: 103 to 105 s−1) equipped with a flow cell (B05 sensor type, 50 μm cell depth).

Experimental Example 1: Comparison of Stability Depending on Type of Amino Acid

Regarding the liquid pharmaceutical formulations used in Experimental Example 1, each buffer solution was prepared so as to be adapted for the corresponding pH, added with various amino acids, further added with an antibody, and further added with a surfactant, thus yielding the samples set forth in Table 1 below. The specific content of each component was as described in Table 1 below. The total volume was 3 mL.

TABLE 1

| Classification | Antibody content (mg/mL) | Surfactant | Sugar alcohol or NaCl | Buffer solution | pH | Amino acid |
|---|---|---|---|---|---|---|
| Example 1 | 200 | Polysorbate 80 0.05% (w/v) | Sorbitol 5% (w/v) | Sodium acetate 25 mM | 5.0 | Methionine 10 mM |
| Example 2 | 200 | Polysorbate 80 0.05% (w/v) | Sorbitol 5% (w/v) | Sodium acetate 25 mM | 5.0 | Proline 87 mM |
| Example 3 | 200 | Polysorbate 80 0.05% (w/v) | Sorbitol 5% (w/v) | Sodium acetate 25 mM | 5.0 | Aspartic acid 10 mM |

The liquid pharmaceutical formulations prepared in Examples 1 to 3 were measured for stability after 0 weeks, 3 weeks, and 7 weeks at a temperature of 5±3° C., and for stability after 3 weeks and 7 weeks at a temperature of 40±2° C. and a relative humidity of 75±5%. The results thereof are shown in Tables 2 to 8 below.

Low-Molecular-Weight Component Content

TABLE 2

| Classification | After 0 weeks at 5 ± 3° C. | After 7 weeks at 5 ± 3° C. | After 3 weeks at 40 ± 2° C. | After 7 weeks at 40 ± 2° C. |
|---|---|---|---|---|
| Example 1 | 0.0 | 0.1 | 0.5 | 1.1 |
| Example 2 | 0.0 | 0.1 | 0.6 | 1.2 |
| Example 3 | 0.0 | 0.1 | 0.8 | 1.7 |

As is apparent from Table 2, Example 1 included 1.1% or less of the low-molecular-weight component after 7 weeks at a temperature of 40° C.

Main Component Content

TABLE 3

| Classification | After 0 weeks at 5 ± 3° C. | After 7 weeks at 5 ± 3° C. | After 3 weeks at 40 ± 2° C. | After 7 weeks at 40 ± 2° C. |
|---|---|---|---|---|
| Example 1 | 99.4 | 99.3 | 98.1 | 97.1 |
| Example 2 | 99.4 | 99.3 | 98.0 | 97.0 |
| Example 3 | 99.5 | 99.3 | 98.0 | 96.7 |

As is apparent from Table 3, Example 1 included 97.1% or more of the main component after 7 weeks at a temperature of 40° C.

Intact Immunoglobulin G Content (Intact IgG %)

TABLE 4

| Classification | After 0 weeks at 5 ± 3° C. | After 7 weeks at 5 ± 3° C. | After 3 weeks at 40 ± 2° C. | After 7 weeks at 40 ± 2° C. |
|---|---|---|---|---|
| Example 1 | 97.6 | 97.1 | 95.4 | 92.5 |
| Example 2 | 97.6 | 97.1 | 95.2 | 91.9 |
| Example 3 | 97.2 | 97.0 | 94.6 | 90.4 |

As is apparent from Table 4, the intact immunoglobulin G content of Example 1 after 7 weeks at a temperature of 40° C. was 92.5% or more, which was evaluated to be high compared to Examples 2 and 3.

Intact Heavy-Chain and Light-Chain Content (Intact HC+LC %)

TABLE 5

| Classification | After 0 weeks at 5 ± 3° C. | After 7 weeks at 5 ± 3° C. | After 3 weeks at 40 ± 2° C. | After 7 weeks at 40 ± 2° C. |
|---|---|---|---|---|
| Example 1 | 99.4 | 98.8 | 99.2 | 97.3 |
| Example 2 | 99.4 | 98.8 | 98.1 | 97.2 |
| Example 3 | 99.4 | 98.8 | 99.1 | 96.8 |

As is apparent from Table 5, the intact heavy-chain and light-chain content of Example 1 after 7 weeks at a temperature of 40° C. was 97.3% or more, which was evaluated to be high compared to Examples 2 and 3.

Oxidation Rate (Heavy-Chain Met 255)

TABLE 6

| Classification | After 0 weeks at 5 ± 3° C. | After 7 weeks at 5 ± 3° C. | After 3 weeks at 40 ± 2° C. | After 7 weeks at 40 ± 2° C. |
|---|---|---|---|---|
| Example 1 | 2.7 | 2.5 | 2.8 | 3.1 |
| Example 2 | 2.7 | 3.0 | 4.1 | 5.1 |
| Example 3 | 2.8 | 3.0 | 4.0 | 5.7 |

As is apparent from Table 6, Example 1 exhibited the lowest oxidation rate of heavy-chain Met 255 under all conditions. In particular, the oxidation rate of heavy-chain Met 255 of Example 1 after 7 weeks at a temperature of 40° C. was 3.1% or less, which was evaluated to be low compared to Examples 2 and 3.

Charge Variant (Main Peak)

TABLE 7

| Classification | After 0 weeks at 5 ± 3° C. | After 7 weeks at 5 ± 3° C. | After 3 weeks at 40 ± 2° C. | After 7 weeks at 40 ± 2° C. |
|---|---|---|---|---|
| Example 1 | 59.7 | 53.1 | 27.6 | 21.5 |
| Example 2 | 59.7 | 52.9 | 27.0 | 20.1 |
| Example 3 | 59.8 | 52.5 | 23.8 | 15.4 |

As is apparent from Table 7, Example 1 exhibited the highest main peak under all conditions. In particular, the main peak of Example 1 after 7 weeks at a temperature of 40° C. was 21.5% or more, which was evaluated to be the highest.

Number of subvisible particles (1.00 μm≤, <100.00 μm)

TABLE 8

| Classification | After 0 weeks at 5 ± 3° C. | After 7 weeks at 5 ± 3° C. | After 7 weeks at 40 ± 2° C. |
|---|---|---|---|
| Example 1 | 225 | 530 | 44 |
| Example 2 | 221 | 29 | 239 |
| Example 3 | 293 | 155 | 53 |

As is apparent from Table 8, the number of subvisible particles (1.00 μm≤, <100.00 μm) of Example 1 after 7 weeks at a temperature of 40° C. was the lowest.

Experimental Example 2: Comparison of Stability Depending on Type of Sugar Alcohol, pH, and Type of Surfactant Regarding the liquid pharmaceutical formulations used in Experimental Example 2, each buffer solution was prepared so as to be adapted for the corresponding pH, added with a sugar alcohol, further added with an antibody, and further added with a surfactant, thus yielding the samples set forth in Table 9 below. The concentration of each component was as described in Table 9 below. The total volume was 3 mL.

TABLE 9

| Classi-fication | Antibody content (mg/mL) | Surfactant | Sugar alcohol or NaCl | Buffer solution | pH |
|---|---|---|---|---|---|
| Example 4 | 200 | Polysorbate 80 0.05% (w/v) | Sorbitol 5% (w/v) | Sodium acetate 25 mM | 5.0 |
| Example 5 | 200 | Polysorbate 80 0.05% (w/v) | Mannitol 5% (w/v) | Sodium acetate 25 mM | 5.0 |
| Example 6 | 200 | Polysorbate 80 0.05% (w/v) | Trehalose 10% (w/v) | Sodium acetate 25 mM | 5.0 |

TABLE 9-continued

| Classi-fication | Antibody content (mg/mL) | Surfactant | Sugar alcohol or NaCl | Buffer solution | pH |
|---|---|---|---|---|---|
| Example 7 | 200 | Polysorbate 80 0.05% (w/v) | Sucrose 10% (w/v) | Sodium acetate 25 mM | 5.0 |
| Example 8 | 200 | Polysorbate 80 0.05% (w/v) | Sorbitol 5% (w/v) | Sodium acetate 25 mM | 5.5 |
| Example 9 | 200 | Polysorbate 20 0.05% (w/v) | Sorbitol 5% (w/v) | Sodium acetate 25 mM | 5.0 |

The above formulations were measured for stability after 0 weeks, 3 weeks, and 7 weeks at a temperature of 5±3° C., and for stability after 3 weeks and 7 weeks at a temperature of 40±2° C. and a relative humidity of 75±5%. The results thereof are shown in Tables 10 to 20 below.

Type of Sugar Alcohol

Turbidity

TABLE 10

| Classi-fication | After 0 weeks at 5 ± 3° C. | After 0 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 0.0045 | 0.0040 | 0.0030 | 0.0020 | 0.0040 |
| Example 5 | 0.0045 | 0.0040 | 0.0040 | 0.0035 | 0.0040 |
| Example 6 | 0.0050 | 0.0040 | 0.0040 | 0.0045 | 0.0030 |
| Example 7 | 0.0070 | 0.0050 | 0.0040 | 0.0040 | 0.0050 |

As is apparent from Table 10, when sorbitol, mannitol, trehalose, or sucrose was used as the sugar alcohol, the absorbance was 0.0050 or less, even after 7 weeks at 40° C.

Main Component Content

TABLE 11

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 99.4 | 99.3 | 99.3 | 98.0 | 96.8 |
| Example 5 | 99.4 | 99.4 | 99.3 | 97.9 | 96.8 |
| Example 6 | 99.4 | 99.3 | 99.3 | 98.0 | 96.8 |
| Example 7 | 99.3 | 99.2 | 99.2 | 97.9 | 96.7 |

As is apparent from Table 11, when sorbitol, mannitol, trehalose, or sucrose was used as the sugar alcohol, the main component content was 96.7% or more, even after 7 weeks at 40° C.

Low-Molecular-Weight Component Content

TABLE 12

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 0.0 | 0.0 | 0.1 | 0.6 | 1.3 |
| Example 5 | 0.0 | 0.0 | 0.1 | 0.6 | 1.3 |
| Example 6 | 0.0 | 0.0 | 0.0 | 0.5 | 1.2 |
| Example 7 | 0.0 | 0.0 | 0.1 | 0.5 | 1.0 |

As is apparent from Table 12, when sorbitol, mannitol, trehalose, or sucrose was used as the sugar alcohol, the low-molecular-weight component content was 1.3% or less, even after 7 weeks at 40° C.

Intact Heavy-Chain and Light-Chain Content (Intact HC+LC %)

TABLE 13

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 99.4 | 99.6 | 98.9 | 99.1 | 97.0 |
| Example 5 | 99.4 | 99.6 | 98.9 | 99.2 | 97.0 |
| Example 6 | 99.2 | 99.6 | 98.9 | 99.1 | 97.1 |
| Example 7 | 99.4 | 99.6 | 98.8 | 99.2 | 97.2 |

As is apparent from Table 13, when sorbitol, mannitol, trehalose or sucrose was used as the sugar alcohol, the intact heavy-chain and light-chain content was 97.0% or more after 7 weeks at a temperature of 40° C.

Oxidation Rate (Heavy-Chain Met 255)

TABLE 14

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 3.3 | 2.8 | 2.8 | 3.8 | 5.0 |
| Example 5 | 2.8 | 2.7 | 2.9 | 3.7 | 4.9 |
| Example 6 | 2.7 | 2.7 | 2.9 | 3.8 | 5.0 |
| Example 7 | 3.3 | 2.7 | 2.7 | 3.8 | 4.9 |

As is apparent from Table 14, when sorbitol, mannitol, trehalose, or sucrose was used as the sugar alcohol, the oxidation rate of heavy-chain Met 255 was 5.0% or less after 7 weeks at a temperature of 40° C.

pH

Turbidity

TABLE 15

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 0.0045 | 0.0040 | 0.0030 | 0.0020 | 0.0040 |
| Example 8 | 0.0060 | 0.0020 | 0.0030 | 0.0020 | 0.0030 |

As is apparent from Table 15, when the pH was 5.0 to 5.5, the absorbance was 0.0040 or less, even after 7 weeks at 40° C.

Main Component Content

TABLE 16

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 99.4 | 99.3 | 99.3 | 98.0 | 96.8 |
| Example 8 | 99.3 | 99.2 | 99.1 | 97.8 | 96.6 |

As is apparent from Table 16, when the pH was 5.0 to 5.5, the main component content was 96.6% or more, even after 7 weeks at 40° C.

Low-Molecular-Weight Component Content

TABLE 17

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 0.0 | 0.0 | 0.1 | 0.6 | 1.3 |
| Example 8 | 0.0 | 0.0 | 0.1 | 0.5 | 1.0 |

As is apparent from Table 17, when the pH was 5.0 to 5.5, the low-molecular-weight component content was 1.3% or less, even after 7 weeks at 40° C.

Intact Immunoglobulin G Content (Intact IgG %)

TABLE 18

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 96.3 | 97.4 | 97.0 | 95.2 | 91.8 |
| Example 8 | 97.7 | 97.4 | 97.1 | 95.4 | 92.5 |

As is apparent from Table 18, when the pH was 5.0 to 5.5, the intact immunoglobulin G content was 91.8% or more, even after 7 weeks at 40° C.

Intact Heavy-Chain and Light-Chain Content (Intact HC+LC %)

TABLE 19

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 99.4 | 99.6 | 98.9 | 99.1 | 97.0 |
| Example 8 | 99.4 | 99.6 | 98.8 | 99.2 | 97.2 |

As is apparent from Table 19, when the pH was 5.0 to 5.5, the intact heavy-chain and light-chain content was 97.0% or more after 7 weeks at 40° C.

Oxidation Rate (Heavy-Chain Met 255)

TABLE 20

| Classi-fication | After 0 weeks at 5 ± 3° C. | After 3 weeks at 5 ± 3° C. | After 7 weeks at 5 ± 3° C. | After 3 weeks at 40 ± 2° C. | After 7 weeks at 40 ± 2° C. |
|---|---|---|---|---|---|
| Example 4 | 3.3 | 2.8 | 2.8 | 3.8 | 5.0 |
| Example 8 | 2.8 | 2.7 | 2.9 | 3.8 | 5.1 |

As is apparent from Table 20, when the pH was 5.0 to 5.5, the oxidation rate of heavy-chain Met 255 was 5.1% or less after 7 weeks at 40° C.

Type of Surfactant

Subvisible particles (10.00 μm≤, <100.00 μm)

TABLE 21

| Classification | Surfactant | After 0 weeks at 5° C. | After 3 weeks at 5° C. | After 7 weeks at 5° C. | After 3 weeks at 40° C. | After 7 weeks at 40° C. |
|---|---|---|---|---|---|---|
| Example 4 | Polysorbate 80 0.05% (w/v) | 32 | 6 | 15 | 42 | 2 |
| Example 9 | Polysorbate 20 0.05% (w/v) | 3 | 12 | 0 | 11 | 9 |

As is apparent from Table 21, when Polysorbate 80 or Polysorbate 20 was used as the surfactant, the number of subvisible particles (10.00 μm≤, <100.00 μm) was 10 or less after 7 weeks at 40° C.

Experimental Example 3: Comparison of Stability Depending on Concentration of Protein, Sugar Alcohol, Amino Acid, and Surfactant Regarding the liquid pharmaceutical formulations used in Experimental Example 3, each buffer solution was prepared at a pH of 5.0 using sodium acetate, added with sorbitol as a sugar alcohol, further added with amino acid, further added with an antibody, and further added with a surfactant, thus yielding the samples set forth in Table 22 below. The content of each component was as described in Table 22 below. The total volume was 3 mL.

TABLE 22

| Classification | Antibody content (mg/mL) | Surfactant | Sugar | Buffer solution | pH | Amino acid |
|---|---|---|---|---|---|---|
| Example 1 | 200 | Polysorbate 80 0.05% (w/v) | Sorbitol 5% (w/v) | Sodium acetate 25 mM | 5.0 | Methionine 10 mM |
| Example 10 | 200 | Polysorbate 80 0.05% (w/v) | Sorbitol 4.5% (w/v) | Sodium acetate 25 mM | 5.0 | Methionine 10 mM |

TABLE 22-continued

| Classification | Antibody content (mg/mL) | Surfactant | Sugar | Buffer solution | pH | Amino acid |
|---|---|---|---|---|---|---|
| Example 11 | 180 | Polysorbate 80 0.05% (w/v) | Sorbitol 4.5% (w/v) | Sodium acetate 25 mM | 5.0 | Methionine 10 mM |
| Example 12 | 220 | Polysorbate 80 0.05% (w/v) | Sorbitol 4.5% (w/v) | Sodium acetate 25 mM | 5.0 | Methionine 10 mM |
| Example 13 | 200 | Polysorbate 80 0.05% (w/v) | Sorbitol 4% (w/v) | Sodium acetate 25 mM | 5.0 | Methionine 10 mM |
| Example 14 | 200 | Polysorbate 80 0.05% (w/v) | Sorbitol 4.5% (w/v) | Sodium acetate 25 mM | 5.0 | Methionine 5 mM |
| Example 15 | 200 | Polysorbate 80 0.05% (w/v) | Sorbitol 4.5% (w/v) | Sodium acetate 25 mM | 5.0 | Methionine 15 mM |
| Example 16 | 200 | Polysorbate 80 0.02% (w/v) | Sorbitol 4.5% (w/v) | Sodium acetate 25 mM | 5.0 | Methionine 10 mM |
| Example 17 | 200 | Polysorbate 80 0.08% (w/v) | Sorbitol 4.5% (w/v) | Sodium acetate 25 mM | 5.0 | Methionine 10 mM |

The above formulations were measured for stability after 0 weeks, 3 weeks, and 6 weeks at a temperature of 5±3° C., stability after 3 weeks and 6 weeks at a temperature of 25±2° C. and a relative humidity of 60±5%, and stability after 3 and 6 weeks at a temperature of 40±2° C. and a relative humidity of 75±5%. The results thereof are shown in Tables 23 to 53 below.

Concentration of Protein

High-Molecular-Weight Component Content

TABLE 23

| Classification | Antibody content (mg/mL) | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | 200 | 0.5 | 0.5 | 0.5 | 0.8 | 0.8 | 1.3 | 1.5 |
| Example 11 | 180 | 0.4 | 0.5 | 0.5 | 0.7 | 0.7 | 1.1 | 1.3 |
| Example 12 | 220 | 0.5 | 0.6 | 0.5 | 0.8 | 0.9 | 1.4 | 1.7 |

As is apparent from Table 23, the high-molecular-weight component content increased with an increase in the antibody concentration, but the high-molecular-weight component content was generally low after 6 weeks at 5° C., 25° C. and 40° C. within the antibody concentration range of 180 to 220 mg/mL.

Main Component Content

TABLE 24

| Classification | Antibody content (mg/mL) | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | 200 | 99.5 | 99.4 | 99.4 | 99.1 | 99.0 | 98.2 | 97.5 |
| Example 11 | 180 | 99.6 | 99.5 | 99.5 | 99.2 | 99.1 | 98.3 | 97.6 |
| Example 12 | 220 | 99.5 | 99.4 | 99.4 | 99.0 | 98.9 | 98.1 | 97.3 |

As is apparent from Table 24, the main component content decreased with an increase in the antibody concentration, but the main component content was generally high after 6 weeks at 5° C., 25° C. and 40° C. within the antibody concentration range of 180 to 220 mg/mL.

Low-Molecular-Weight Component Content

TABLE 25

| Classification | Antibody content (mg/mL) | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | 200 | 0.0 | 0.1 | 0.1 | 0.1 | 0.2 | 0.6 | 1.0 |
| Example 11 | 180 | 0.0 | 0.1 | 0.1 | 0.1 | 0.2 | 0.6 | 1.1 |
| Example 12 | 220 | 0.0 | 0.1 | 0.0 | 0.1 | 0.2 | 0.6 | 1.0 |

As is apparent from Table 25, the low-molecular-weight component content was generally low after 6 weeks at 5° C., 25° C. and 40° C. within the antibody concentration range of 180 to 220 mg/mL.

Intact Immunoglobulin G Content (Intact IgG %)

TABLE 26

| Classification | Antibody content (mg/mL) | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | 200 | 98.2 | 97.6 | 97.0 | 97.3 | 96.3 | 95.7 | 91.4 |
| Example 11 | 180 | 98.2 | 97.6 | 97.1 | 97.3 | 96.2 | 95.7 | 91.4 |
| Example 12 | 220 | 98.2 | 97.6 | 97.0 | 97.2 | 96.1 | 95.7 | 91.4 |

As is apparent from Table 26, the intact immunoglobulin G content was generally high after 6 weeks at 5° C., 25° C., and 40° C. within the antibody concentration range of 180 to 220 mg/mL.

Intact Heavy-Chain and Light-Chain Content (Intact HC+LC %)

TABLE 27

| Classification | Antibody content (mg/mL) | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | 200 | 99.5 | 99.3 | 99.4 | 99.3 | 99.2 | 99.0 | 98.5 |
| Example 11 | 180 | 99.5 | 99.4 | 99.4 | 99.3 | 99.2 | 99.0 | 98.3 |
| Example 12 | 220 | 99.5 | 99.4 | 99.4 | 99.3 | 99.2 | 98.9 | 98.3 |

As is apparent from Table 27, the intact heavy-chain and light-chain content was generally high after 6 weeks at 5° C., 25° C., and 40° C. within the antibody concentration range of 180 to 220 mg/mL.

Oxidation Rate (Heavy-Chain Met 255)

TABLE 28

| Classification | Antibody content (mg/mL) | After 0 weeks at 5 ± 3° C. | After 6 weeks at 5 ± 3° C. | After 6 weeks at 25 ± 2° C. | After 6 weeks at 40 ± 2° C. |
|---|---|---|---|---|---|
| Example 10 | 200 | 1.8 | 2.1 | 2.2 | 2.5 |
| Example 11 | 180 | 1.7 | 2.1 | 2.1 | 2.4 |
| Example 12 | 220 | 1.9 | 2.0 | 2.1 | 2.4 |

As is apparent from Table 28, the oxidation rate of heavy-chain Met 255 was generally low, specifically 2.5% or less, after 6 weeks at 5° C., 25° C., and 40° C. within the antibody concentration range of 180 to 220 mg/mL.

Number of Subvisible Particles (10.00 µm≤, <100.00 µm)

TABLE 29

| Classification | Antibody content (mg/mL) | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | 200 | 27 | 18 | 21 | 6 | 31 | 0 | 17 |
| Example 11 | 180 | 6 | 5 | 15 | 0 | 13 | 10 | 136 |
| Example 12 | 220 | 0 | 37 | 8 | 4 | 5 | 0 | 59 |

As is apparent from Table 29, the number of subvisible particles (10.00 µm≤, <100.00 µm) was 200 or less after 6 weeks at 5° C., 25° C. and 40° C. within the antibody concentration range of 180 to 220 mg/mL.

Concentration of Sugar Alcohol
High-Molecular-Weight Component Content

TABLE 30

| Classification | Sugar alcohol content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 1 | Sorbitol 5% (w/v) | 0.5 | 0.5 | 0.5 | 0.8 | 0.8 | 1.2 | 1.5 |
| Example 10 | Sorbitol 4.5% (w/v) | 0.5 | 0.5 | 0.5 | 0.8 | 0.8 | 1.3 | 1.5 |
| Example 13 | Sorbitol 4% (w/v) | 0.5 | 0.5 | 0.5 | 0.8 | 0.8 | 1.2 | 1.5 |

As is apparent from Table 30, the high-molecular-weight component content was generally low after 6 weeks at 5° C., 25° C., and 40° C. within the sugar alcohol sorbitol concentration range of 4% to 5%.

Main Component Content

TABLE 31

| Classification | Sugar alcohol content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 1 | Sorbitol 5% (w/v) | 99.5 | 99.4 | 99.5 | 99.1 | 99.0 | 98.2 | 97.5 |
| Example 10 | Sorbitol 4.5% (w/v) | 99.5 | 99.4 | 99.4 | 99.1 | 99.0 | 98.2 | 97.5 |
| Example 13 | Sorbitol 4% (w/v) | 99.5 | 99.4 | 99.5 | 99.1 | 99.0 | 98.2 | 97.5 |

As is apparent from Table 31, the main component content was generally high after 6 weeks at 5° C., 25° C., and 40° C. within the sugar alcohol sorbitol concentration range of 4% to 5%.

Low-Molecular-Weight Component Content

TABLE 32

| Classification | Sugar alcohol content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 1 | Sorbitol 5% (w/v) | 0.0 | 0.1 | 0.1 | 0.1 | 0.2 | 0.6 | 1.0 |
| Example 10 | Sorbitol 4.5% (w/v) | 0.0 | 0.1 | 0.1 | 0.1 | 0.2 | 0.6 | 1.0 |
| Example 13 | Sorbitol 4% (w/v) | 0.0 | 0.1 | 0.1 | 0.1 | 0.2 | 0.6 | 1.0 |

As is apparent from Table 32, the low-molecular-weight component content was generally low after 6 weeks at 5° C., 25° C., and 40° C. within the sugar alcohol sorbitol concentration range of 4% to 5%.

Intact Immunoglobulin G Content (Intact IgG %)

TABLE 33

| Classification | Sugar alcohol content | After 0 weeks at 5 ± 3° C. | After 3 weeks at 5 ± 3° C. | After 6 weeks at 5 ± 3° C. | Alter 3 weeks at 25 ± 2° C. | After 6 weeks at 25 ± 2° C. | Alter 3 weeks at 40 ± 2° C. | After 6 weeks at 40 ± 2° C. |
|---|---|---|---|---|---|---|---|---|
| Example 1 | Sorbitol 5% (w/v) | 98.2 | 97.6 | 97.1 | 97.3 | 95.8 | 95.8 | 91.5 |
| Example 10 | Sorbitol 4.5% (w/v) | 98.2 | 97.6 | 97.0 | 97.3 | 96.3 | 95.7 | 91.4 |
| Example 13 | Sorbitol 4% (w/v) | 98.2 | 97.6 | 97.1 | 97.3 | 95.6 | 95.6 | 91.4 |

As is apparent from Table 33, the intact immunoglobulin G content was generally high after 6 weeks at 5° C., 25° C., and 40° C. within the sugar alcohol sorbitol concentration range of 4% to 5%.

Intact Heavy-Chain and Light-Chain Content (Intact HC+LC %)

TABLE 34

| Classification | Sugar alcohol content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 1 | Sorbitol 5% (w/v) | 99.4 | 99.4 | 99.3 | 99.3 | 99.2 | 99.0 | 98.4 |
| Example 10 | Sorbitol 4.5% (w/v) | 99.5 | 99.3 | 99.4 | 99.3 | 99.2 | 99.0 | 98.5 |
| Example 13 | Sorbitol 4% (w/v) | 99.5 | 99.3 | 99.3 | 99.3 | 99.2 | 98.9 | 98.5 |

As is apparent from Table 34, the intact heavy-chain and light-chain content was generally high after 6 weeks at 5° C., 25° C. and 40° C. within the sugar alcohol sorbitol concentration range of 4% to 5%.

Oxidation Rate (Heavy-Chain Met 255)

TABLE 35

| Classification | Sugar alcohol content | After 0 weeks at 5 ± 3° C. | After 6 weeks at 5 ± 3° C. | After 6 weeks at 25 ± 2° C. | After 6 weeks at 40 ± 2° C. |
|---|---|---|---|---|---|
| Example 1 | Sorbitol 5% (w/v) | 1.8 | 2.0 | 2.1 | 2.4 |
| Example 10 | Sorbitol 4.5% (w/v) | 1.8 | 2.1 | 2.2 | 2.5 |
| Example 13 | Sorbitol 4% (w/v) | 1.8 | 2.0 | 2.1 | 2.3 |

As is apparent from Table 35, the oxidation rate of heavy-chain Met 255 was generally low, specifically 2.5% or less, after 6 weeks at 5° C., 25° C., and 40° C. within the sugar alcohol sorbitol concentration range of 4% to 5%.

Number of Subvisible Particles (10.00 μm≤, <100.00 μm)

TABLE 36

| Classification | Sugar alcohol content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 1 | Sorbitol 5% (w/v) | 5 | 0 | 10 | 20 | 10 | 8 | 21 |
| Example 10 | Sorbitol 4.5% (w/v) | 27 | 117 | 21 | 6 | 31 | 0 | 17 |
| Example 13 | Sorbitol 4% (w/v) | 7 | 29 | 0 | 16 | 12 | 60 | 8 |

As is apparent from Table 36, the number of subvisible particles (10.00 μm≤, <100.00 μm) was 200 or less after 6 weeks at 5° C., 25° C. and 40° C. within the sugar alcohol sorbitol concentration range of 4% to 5%.

Viscosity (cP)

TABLE 37

| Classification | Sugar alcohol content | After 0 weeks at 5 ± 3° C. |
|---|---|---|
| Example 1 | Sorbitol 5% (w/v) | 13.7 |
| Example 10 | Sorbitol 4.5% (w/v) | 12.2 |
| Example 13 | Sorbitol 4% (w/v) | 12.8 |

As is apparent from Table 37, the viscosity was 14 cp or less after 0 weeks at 5° C. within the sugar alcohol sorbitol concentration range of 4% to 5%.

Concentration of Amino Acid

High-Molecular-Weight Component Content

TABLE 38

| Classification | Amino acid content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | Methionine 10 mM | 0.5 | 0.5 | 0.5 | 0.8 | 0.8 | 1.3 | 1.5 |
| Example 14 | Methionine 5 mM | 0.5 | 0.5 | 0.5 | 0.8 | 0.8 | 1.3 | 1.8 |
| Example 15 | Methionine 15 mM | 0.4 | 0.5 | 0.5 | 0.7 | 0.8 | 1.2 | 1.5 |

As is apparent from Table 38, the high-molecular-weight component content was generally low after 6 weeks at 5° C., 25° C. and 40° C. within the methionine concentration range of 5 mM to 15 mM.

Main Component Content

TABLE 39

| Classification | Amino acid content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | Methionine 10 mM | 99.5 | 99.4 | 99.4 | 99.1 | 99.0 | 98.2 | 97.5 |
| Example 14 | Methionine 5 mM | 99.5 | 99.4 | 99.5 | 99.1 | 99.0 | 98.2 | 97.2 |
| Example 15 | Methionine 15 mM | 99.5 | 99.4 | 99.5 | 99.1 | 99.0 | 98.3 | 97.5 |

As is apparent from Table 39, the main component content was generally high after 6 weeks at 5° C., 25° C., and 40° C. within the methionine concentration range of 5 mM to 15 mM.

Low-Molecular-Weight Component Content

TABLE 40

| Classification | Amino acid content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | Methionine 10 mM | 0.0 | 0.1 | 0.1 | 0.1 | 0.2 | 0.6 | 1.0 |
| Example 14 | Methionine 5 mM | 0.1 | 0.1 | 0.1 | 0.1 | 0.2 | 0.6 | 1.0 |
| Example 15 | Methionine 15 mM | 0.0 | 0.1 | 0.0 | 0.1 | 0.2 | 0.6 | 1.0 |

As is apparent from Table 40, the low-molecular-weight component content was generally low after 6 weeks at 5° C., 25° C., and 40° C. within the methionine concentration range of 5 mM to 15 mM.

Intact Immunoglobulin G Content (Intact IgG %)

TABLE 41

| Classification | Amino acid content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | Methionine 10 mM | 98.2 | 97.6 | 97.0 | 97.3 | 96.3 | 95.7 | 91.4 |

TABLE 41-continued

| Classification | Amino acid content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 14 | Methionine 5 mM | 98.2 | 97.5 | 97.2 | 97.3 | 96.1 | 95.7 | 92.0 |
| Example 15 | Methionine 15 mM | 98.0 | 97.6 | 97.2 | 97.3 | 96.0 | 95.7 | 92.1 |

As is apparent from Table 41, the intact immunoglobulin G component content was generally high after 6 weeks at 5° C., 25° C. and 40° C. within the methionine concentration range of 5 mM to 15 mM.

Intact Heavy-Chain and Light-Chain Content (Intact HC+LC %)

TABLE 42

| Classification | Amino acid content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | Methionine 10 mM | 99.5 | 99.3 | 99.4 | 99.3 | 99.2 | 99.0 | 98.5 |
| Example 14 | Methionine 5 mM | 99.4 | 99.4 | 99.4 | 99.3 | 99.1 | 98.9 | 98.4 |
| Example 15 | Methionine 15 mM | 99.5 | 99.3 | 99.3 | 99.3 | 99.1 | 98.9 | 98.5 |

As is apparent from Table 42, the intact heavy-chain and light-chain content was generally high after 6 weeks at 5° C., 25° C. and 40° C. within the methionine concentration range of 5 mM to 15 mM.

Oxidation Rate (Heavy-Chain Met 255)

TABLE 43

| Classification | Amino acid content | After 0 weeks at 5 ± 3° C. | After 6 weeks at 5 ± 3° C. | After 6 weeks at 25 ± 2° C. | After 6 weeks at 40 ± 2° C. |
|---|---|---|---|---|---|
| Example 10 | Methionine 10 mM | 1.8 | 2.1 | 2.2 | 2.5 |
| Example 14 | Methionine 5 mM | 1.8 | 2.0 | 2.1 | 2.6 |
| Example 15 | Methionine 15 mM | 1.7 | 2.0 | 2.1 | 2.2 |

As is apparent from Table 43, the oxidation rate of heavy-chain Met 255 was generally low, specifically 2.6% or less, after 6 weeks at 5° C., 25° C. and 40° C. within the methionine concentration range of 5 mM to 15 mM.

Number of Subvisible Particles (10.00 μm≤, <100.00 μm)

TABLE 44

| Classification | Amino acid content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | Methionine 10 mM | 27 | 18 | 21 | 6 | 31 | 35 | 17 |
| Example 14 | Methionine 5 mM | 6 | 3 | 9 | 18 | 17 | 8 | 4 |
| Example 15 | Methionine 15 mM | 12 | 6 | 7 | 6 | 6 | 18 | 6 |

As is apparent from Table 44, the number of subvisible particles (10.00 μm≤, <100.00 μm) was 100 or less after 6 weeks at 5° C., 25° C. and 40° C. within the methionine concentration range of 5 mM to 15 mM.

Viscosity (cP)

TABLE 45

| Classification | Amino acid content | After 0 weeks at 5 ± 3° C. |
| --- | --- | --- |
| Example 10 | Methionine 10 mM | 13.7 |
| Example 14 | Methionine 5 mM | 13.2 |
| Example 15 | Methionine 15 mM | 13.2 |

As is apparent from Table 45, the viscosity was 14 cP or less after 0 weeks at 5° C. within the methionine concentration range of 5 mM to 15 mM.

Concentration of Surfactant

High-Molecular-Weight Component Content

TABLE 46

| Classification | Surfactant content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
| --- | --- | --- | --- | --- | --- | --- | --- | --- |
| Example 10 | Polysorbate 80 0.05% (w/v) | 0.5 | 0.5 | 0.5 | 0.8 | 0.8 | 1.3 | 1.5 |
| Example 16 | Polysorbate 80 0.02% (w/v) | 0.5 | 0.5 | 0.5 | 0.8 | 0.8 | 1.2 | 1.5 |
| Example 17 | Polysorbate 80 0.08% (w/v) | 0.5 | 0.5 | 0.5 | 0.8 | 0.8 | 1.2 | 1.6 |

As is apparent from Table 46, the high-molecular-weight component content was generally low after 6 weeks at 5° C., 25° C., and 40° C. within the polysorbate concentration range of 0.02% to 0.08%.

Main Component Content

TABLE 47

| Classification | Surfactant content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
| --- | --- | --- | --- | --- | --- | --- | --- | --- |
| Example 10 | Polysorbate 80 0.05% (w/v) | 99.5 | 99.4 | 99.4 | 99.1 | 99.0 | 98.2 | 97.5 |
| Example 16 | Polysorbate 80 0.02% (w/v) | 99.5 | 99.4 | 99.5 | 99.1 | 99.0 | 98.2 | 97.5 |
| Example 17 | Polysorbate 80 0.08% (w/v) | 99.5 | 99.4 | 99.5 | 99.1 | 98.9 | 98.2 | 97.4 |

As is apparent from Table 47, the main component content was generally high after 6 weeks at 5° C., 25° C., and 40° C. within the polysorbate concentration range of 0.02% to 0.08%.

Low-Molecular-Weight Component Content

TABLE 48

| Classification | Surfactant content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
| --- | --- | --- | --- | --- | --- | --- | --- | --- |
| Example 10 | Polysorbate 80 0.05% (w/v) | 0.0 | 0.1 | 0.1 | 0.1 | 0.2 | 0.6 | 1.0 |
| Example 16 | Polysorbate 80 0.02% (w/v) | 0.0 | 0.0 | 0.0 | 0.1 | 0.2 | 0.6 | 1.0 |
| Example 17 | Polysorbate 80 0.08% (w/v) | 0.0 | 0.1 | 0.0 | 0.1 | 0.2 | 0.6 | 1.0 |

As is apparent from Table 48, the low-molecular-weight component content was generally low after 6 weeks at 5° C., 25° C., and 40° C. within the polysorbate concentration range of 0.02% to 0.08%.

Intact Immunoglobulin G Content (Intact IgG %)

TABLE 49

| Classification | Surfactant content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | Polysorbate 80 0.05% (w/v) | 98.2 | 97.6 | 97.0 | 97.3 | 96.3 | 95.7 | 91.4 |
| Example 16 | Polysorbate 80 0.02% (w/v) | 98.2 | 97.6 | 97.0 | 97.2 | 96.2 | 95.7 | 91.4 |
| Example 17 | Polysorbate 80 0.08% (w/v) | 98.2 | 97.6 | 97.2 | 97.2 | 96.2 | 95.7 | 91.8 |

As is apparent from Table 49, the intact immunoglobulin G component content was generally high after 6 weeks at 5° C., 25° C. and 40° C. within the polysorbate concentration range of 0.02% to 0.08%.

Intact Heavy-Chain and Light-Chain Content (Intact HC+LC %)

TABLE 50

| Classification | Surfactant content | After 0 weeks at 5 ± 3° C. | After 3 weeks at 5 ± 3° C. | After 6 weeks at 5 ± 3° C. | After 3 weeks at 25 ± 2° C. | After 6 weeks at 25 ± 2° C. | After 3 weeks at 40 ± 2° C. | After 6 weeks at 40 ± 2° C. |
|---|---|---|---|---|---|---|---|---|
| Example 10 | Polysorbate 80 0.05% (w/v) | 99.5 | 99.3 | 99.4 | 99.3 | 99.2 | 99.0 | 98.5 |
| Example 16 | Polysorbate 80 0.02% (w/v) | 99.5 | 99.4 | 99.3 | 99.3 | 99.2 | 98.9 | 98.5 |
| Example 17 | Polysorbate 80 0.08% (w/v) | 99.5 | 99.3 | 99.3 | 99.3 | 99.1 | 99.0 | 98.5 |

As is apparent from Table 50, the intact heavy-chain and light-chain content was generally high after 6 weeks at 5° C., 25° C. and 40° C. within the polysorbate concentration range of 0.02% to 0.08%.

Oxidation Rate (Heavy-Chain Met 255)

TABLE 51

| Classification | Surfactant content | After 0 weeks at 5 ± 3° C. | After 6 weeks at 5 ± 3° C. | After 6 weeks at 25 ± 2° C. | After 6 weeks at 40 ± 2° C. |
|---|---|---|---|---|---|
| Example 10 | Polysorbate 80 0.05% (w/v) | 1.8 | 2.1 | 2.2 | 2.5 |
| Example 16 | Polysorbate 80 0.02% (w/v) | 1.8 | 2.0 | 2.1 | 2.4 |
| Example 17 | Polysorbate 80 0.08% (w/v) | 1.5 | 2.1 | 2.1 | 2.5 |

As is apparent from Table 51, the oxidation rate of heavy-chain Met 255 was generally low, specifically 2.5% or less, after 6 weeks at 5° C., 25° C., and 40° C. within the polysorbate concentration range of 0.02% to 0.08%.

Number of Subvisible Particles (10.00 μm≤, <100.00 μm)

TABLE 52

| Classification | Surfactant content | After 0 weeks at 5 ± 3° C. | After 6 weeks at 5 ± 3° C. | After 6 weeks at 25 ± 2° C. | After 6 weeks at 40 ± 2° C. |
|---|---|---|---|---|---|
| Example 10 | Polysorbate 80 0.05% (w/v) | 27 | 21 | 31 | 17 |
| Example 16 | Polysorbate 80 0.02% (w/v) | 62 | 8 | 6 | 23 |
| Example 17 | Polysorbate 80 0.08% (w/v) | 3 | 58 | 31 | 120 |

As is apparent from Table 52, the number of subvisible particles (10.00 μm≤, <100.00 μm) was 200 or less after 6 weeks at 5° C., 25° C. and 40° C. within the polysorbate concentration range of 0.02% to 0.08%.

Viscosity (cP)

TABLE 53

| Classification | Surfactant content | After 0 weeks at 5 ± 3° C. |
|---|---|---|
| Example 10 | Polysorbate 80 0.05% (w/v) | 13.7 |
| Example 16 | Polysorbate 80 0.02% (w/v) | 13.2 |
| Example 17 | Polysorbate 80 0.08% (w/v) | 13.0 |

As is apparent from Table 53, the viscosity was 14 cP or less after 0 weeks at 5° C. within the polysorbate concentration range of 0.02% to 0.08%.

Experimental Example 4: Comparison of Stability Depending on Antibody Concentration, Antibody Substitution, Amino Acid Concentration, Formulation Combination Change and Whether or not Metal Salts are Included Regarding the liquid pharmaceutical formulations used in Experimental Example 4, an experiment was conducted in order to evaluate changes in the stability of the formulation depending on the antibody concentration, substitution of the antibody, the amino acid concentration, some component changes in the formulation combination, and whether or not metal salts are included. To this end, each buffer solution was prepared at a pH of 5.0 using sodium acetate and added with sorbitol as a sugar alcohol, thus yielding the samples set forth in Table 54 below. The content of each component was as described in Table 54 below. The total volume was 3 mL.

TABLE 54

| Classification | Antibody content (mg/mL) | Surfactant | Sugar/Salts | Buffer solution | pH | Amino acid |
|---|---|---|---|---|---|---|
| Example 18 | 100 | Polysorbate 80 0.05% (w/v) | Sorbitol 4.5% (w/v) | Sodium acetate 25 mM | 5.0 | Methionine 10 mM |
| Example 19 | 140 | Polysorbate 80 0.05% (w/v) | Sorbitol 4.5% (w/v) | Sodium acetate 25 mM | 5.0 | Methionine 10 mM |
| Example 20 | 160 | Polysorbate 80 0.05% (w/v) | Sorbitol 4.5% (w/v) | Sodium acetate 25 mM | 5.0 | Methionine 30 mM |
| Example 21 | 160 | Polysorbate 80 0.05% (w/v) | Sorbitol 4.5% (w/v) | Sodium acetate 25 mM | 5.0 | Methionine 10 mM |
| Comparative Example 1 | 160 (different antibody_infliximab) | Polysorbate 80 0.05% (w/v) | Sorbitol 4.5% (w/v) | Sodium acetate 25 mM | 5.0 | Methionine 10 mM |
| Comparative Example 2 | 160 (different antibody_omalizumab) | Polysorbate 80 0.05% (w/v) | Sorbitol 4.5% (w/v) | Sodium acetate 25 mM | 5.0 | Methionine 10 mM |
| Comparative Example 3 | 160 | Polysorbate 80 0.05% (w/v) | — | Sodium acetate 25 mM | 5.0 | Methionine 10 mM |
| Comparative Example 4 | 160 | Polysorbate 80 0.05% (w/v) | Sorbitol 4.5% (w/v) | Sodium acetate 25 mM | 5.0 | — |
| Comparative Example 5 | 160 | Polysorbate 80 0.05% (w/v) | Sodium chloride 140 mM | Sodium acetate 25 mM | 5.0 | Methionine 10 mM |

The above formulations were measured for stability after 0 weeks, 2 weeks, and 4 weeks at a temperature of 5±3° C., and for stability after 2 weeks and 4 weeks at a temperature of 40±2° C. and a relative humidity of 75±5%, and the results thereof are shown in Tables 55 to 82 below.

Concentration of Antibody

Turbidity

TABLE 55

| Classification | Antibody content (mg/mL) | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 18 | 100 | 0.0051 | 0.0050 | 0.0034 | 0.0044 | 0.0025 |
| Example 19 | 140 | 0.0050 | 0.0054 | 0.0045 | 0.0033 | 0.0038 |
| Example 21 | 160 | 0.0020 | 0.0046 | 0.0044 | 0.0030 | 0.0039 |

As is apparent from Table 55, the absorbance was 0.0040 or less after 4 weeks at 5° C. and 40° C. within the antibody concentration range of 100 to 160 mg/mL.

High-Molecular-Weight Component Content

TABLE 56

| Classification | Antibody content (mg/mL) | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 18 | 100 | 0.4 | 0.4 | 0.6 | 0.4 | 0.8 |
| Example 19 | 140 | 0.5 | 0.4 | 0.8 | 0.5 | 1.0 |
| Example 21 | 160 | 0.5 | 0.5 | 0.9 | 0.7 | 1.2 |

As is apparent from Table 56, the high-molecular-weight component content increased with an increase in the antibody concentration, but the high-molecular-weight component content was generally low after 4 weeks at 5° C. and 40° C. within the antibody concentration range of 100 to 160 mg/mL.

Main Component Content

TABLE 57

| Classification | Antibody content (mg/mL) | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 18 | 100 | 99.5 | 99.5 | 98.9 | 99.4 | 98.4 |
| Example 19 | 140 | 99.5 | 99.4 | 98.7 | 99.3 | 98.1 |
| Example 21 | 160 | 99.4 | 99.4 | 98.6 | 99.2 | 97.9 |

As is apparent from Table 57, the main component content decreased with an increase in the antibody concentration, but the main component content was generally high after 4 weeks at 5° C. and 40° C. within the antibody concentration range of 100 to 160 mg/mL.

Low-Molecular-Weight Component Content

TABLE 58

| Classification | Antibody content (mg/mL) | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 18 | 100 | 0.1 | 0.1 | 0.5 | 0.2 | 0.9 |
| Example 19 | 140 | 0.1 | 0.1 | 0.5 | 0.2 | 0.9 |
| Example 21 | 160 | 0.1 | 0.1 | 0.5 | 0.2 | 0.9 |

As is apparent from Table 58, the low-molecular-weight component content was generally low after 4 weeks at 5° C. and 40° C. within the antibody concentration range of 100 to 160 mg/mL.

Intact Immunoglobulin G Content (Intact IgG %)

TABLE 59

| Classification | Antibody content (mg/mL) | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 18 | 100 | 99.0 | 98.3 | 97.4 | 97.2 | 95.1 |
| Example 19 | 140 | 98.9 | 98.5 | 97.3 | 97.2 | 95.0 |
| Example 21 | 160 | 99.0 | 98.1 | 97.4 | 97.0 | 95.0 |

As is apparent from Table 59, the intact immunoglobulin G content was generally high after 4 weeks at 5° C. and 40° C. within the antibody concentration range of 100 to 160 mg/mL.

Intact Heavy-Chain and Light-Chain Content (Intact HC+LC %)

TABLE 60

| Classification | Antibody content (mg/mL) | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 18 | 100 | 99.9 | 99.9 | 99.9 | 99.8 | 99.6 |
| Example 19 | 140 | 99.9 | 99.9 | 99.9 | 99.8 | 99.6 |
| Example 21 | 160 | 99.9 | 99.9 | 99.9 | 99.8 | 99.5 |

As is apparent from Table 60, the intact heavy-chain and light-chain content was generally high after 4 weeks at 5° C. and 40° C. within the antibody concentration range of 100 to 160 mg/mL.

Oxidation Rate (Heavy-Chain Met 255)

TABLE 61

| Classification | Antibody content (mg/mL) | After 0 weeks at 5 ± 3° C. | After 4 weeks at 5 ± 3° C. | After 4 weeks at 40 ± 2° C. |
|---|---|---|---|---|
| Example 18 | 100 | 2.8 | 2.8 | 2.9 |
| Example 19 | 140 | 2.8 | 2.8 | 3.0 |
| Example 21 | 160 | 2.7 | 2.6 | 2.9 |

As is apparent from Table 61, the oxidation rate of heavy-chain Met 255 was generally low, specifically 3.0% or less, after 4 weeks at 5° C. and 40° C. within the antibody concentration range of 100 to 160 mg/mL.

Subvisible Particles (10.00 µm≤, <100.00 µm)

TABLE 62

| Classification | Antibody content (mg/mL) | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 18 | 100 | 3 | 8 | 7 | 41 | 80 |
| Example 19 | 140 | 5 | 2 | 13 | 8 | 26 |
| Example 21 | 160 | 5 | 0 | 7 | 5 | 162 |

As is apparent from Table 62, the number of subvisible particles (10.00 µm≤, <100.00 µm) was 200 or less after 4 weeks at 5° C. and 40° C. within the antibody concentration range of 100 to 160 mg/mL, and thus remained low.

Substitution of Antibody

Viscosity (cP)

TABLE 63

| Classification | Antibody | After 0 weeks at 5 ± 3° C. |
|---|---|---|
| Comparative Example 1 | Different antibody_infliximab | 10.2 |
| Comparative Example 2 | Different antibody_omalizumab | 64.9 |
| Example 21 | trastuzumab | 6.6 |

As is apparent from Table 63, when the antibody trastuzumab was substituted with different antibodies infliximab and omalizumab in the same concentration and formulation, the viscosity was remarkably high and thus decreased stability resulted.

Concentration of Amino Acid

Turbidity

TABLE 64

| Classification | Amino acid content | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 20 | Methionine 30 mM | 0.0026 | 0.0157 | 0.0043 | 0.0035 | 0.0030 |
| Example 21 | Methionine 10 mM | 0.0020 | 0.0046 | 0.0044 | 0.0030 | 0.0039 |

As is apparent from Table 64, the absorbance was 0.0040 or less after 4 weeks at 5° C. and 40° C. within the methionine concentration range of 10 mM to 30 mM.

High-Molecular-Weight Component Content

TABLE 65

| Classification | Amino acid content | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 20 | Methionine 30 mM | 0.5 | 0.5 | 0.9 | 0.6 | 1.2 |
| Example 21 | Methionine 10 mM | 0.5 | 0.5 | 0.9 | 0.7 | 1.2 |

As is apparent from Table 65, the high-molecular-weight component content was generally low after 4 weeks at 5° C. and 40° C. within the methionine concentration range of 10 mM to 30 mM.

Main Component Content

TABLE 66

| Classification | Amino acid content | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 20 | Methionine 30 mM | 99.4 | 99.4 | 98.6 | 99.3 | 97.9 |
| Example 21 | Methionine 10 mM | 99.4 | 99.4 | 98.6 | 99.2 | 97.9 |

As is apparent from Table 66, the main component content was generally high after 4 weeks at 5° C. and 40° C. within the methionine concentration range of 10 mM to 30 mM.

Low-Molecular-Weight Component Content

TABLE 67

| Classification | Amino acid content | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 20 | Methionine 30 mM | 0.1 | 0.1 | 0.5 | 0.2 | 0.9 |
| Example 21 | Methionine 10 mM | 0.1 | 0.1 | 0.5 | 0.2 | 0.9 |

As is apparent from Table 67, the low-molecular-weight component content was generally low after 4 weeks at 5° C. and 40° C. within the methionine concentration range of 10 mM to 30 mM.

Intact Immunoglobulin G Content (Intact IgG %)

TABLE 68

| Classification | Amino acid content | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 20 | Methionine 30 mM | 98.9 | 98.2 | 97.2 | 97.1 | 94.9 |
| Example 21 | Methionine 10 mM | 99.0 | 98.1 | 97.4 | 97.0 | 95.0 |

As is apparent from Table 68, the intact immunoglobulin G content was generally high after 4 weeks at 5° C. and 40° C. in the methionine concentration range of 10 mM to 30 mM.

Intact Heavy-Chain and Light-Chain Content (Intact HC+LC %)

TABLE 69

| Classification | Amino acid content | After 0 weeks at 5 ± 3° C. | After 2 weeks at 5 ± 3° C. | After 4 weeks at 5 ± 3° C. | After 2 weeks at 40±2° C. | After 4 weeks at 40 ± 2° C. |
|---|---|---|---|---|---|---|
| Example 20 | Methionine 30 mM | 99.9 | 99.9 | 99.9 | 99.8 | 99.5 |
| Example 21 | Methionine 10 mM | 99.9 | 99.9 | 99.9 | 99.8 | 99.5 |

As is apparent from Table 69, the intact heavy-chain and light-chain content was generally high after 4 weeks at 5° C. and 40° C. within the methionine concentration range of 10 mM to 30 mM.

Oxidation Rate (Heavy-Chain Met 255)

TABLE 70

| Classification | Amino acid content | After 0 weeks at 5 ± 3° C. | After 4 weeks at 5 ± 3° C. | After 4 weeks at 40 ± 2° C. |
|---|---|---|---|---|
| Example 20 | Methionine 30 mM | 3.0 | 2.9 | 3.3 |
| Example 21 | Methionine 10 mM | 2.7 | 2.6 | 2.9 |

As is apparent from Table 70, the oxidation rate of heavy-chain Met 255 was somewhat high when the concentration of methionine was 30 mM, but the oxidation rate of heavy-chain Met 255 was generally low after 4 weeks at 5° C. and 40° C. within the methionine concentration range of 10 mM to 30 mM.

Subvisible Particles (10.00 μm≤, <100.00 μm)

TABLE 71

| Classification | Amino acid content | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Example 20 | Methionine 30 mM | 15 | 2 | 7 | 9 | 2 |
| Example 21 | Methionine 10 mM | 5 | 0 | 7 | 5 | 162 |

As is apparent from Table 71, the number of subvisible particles (10.00 μm≤, <100.00 μm) was 200 or less after 4 weeks at 5° C. and 40° C. within the methionine concentration range of 10 mM to 30 mM, and thus remained low.

Change in Formulation Combination

High-Molecular-Weight Component Content

TABLE 72

| Classification | Whether or not methionine is included | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Comparative Example 4 | Not included | 0.50 | 0.50 | 0.94 | 0.54 | 1.22 |
| Example 21 | included | 0.50 | 0.49 | 0.90 | 0.67 | 1.17 |

As is apparent from Table 72, the high-molecular-weight component content was lower in Example 21 than in Comparative Example 4 after 4 weeks at 5° C. and 40° C.

Main Component Content

TABLE 73

| Classification | Whether or not methionine is included | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Comparative Example 4 | Not included | 99.40 | 99.36 | 98.54 | 99.28 | 97.88 |
| Example 21 | included | 99.39 | 99.37 | 98.58 | 99.16 | 97.94 |

As is apparent from Table 73, the main component content was higher in Example 21 than in Comparative Example 4 after 4 weeks at 5° C. and 40° C.

Intact Immunoglobulin G Content (Intact IgG %)

TABLE 74

| Classification | Whether or not sorbitol is included | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Comparative Example 3 | Not included | 98.84 | 98.14 | 97.23 | 97.04 | 94.64 |
| Example 21 | Included | 98.95 | 98.10 | 97.35 | 97.01 | 94.95 |

As is apparent from Table 74, the intact immunoglobulin G content was higher in Example 21 than in Comparative Example 3 after 4 weeks at 5° C. and 40° C.

Intact Heavy-Chain and Light-Chain Content (Intact HC+LC %)

TABLE 75

| Classification | Whether or not sorbitol is included | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Comparative Example 3 | Not included | 99.92 | 99.91 | 99.91 | 99.81 | 99.46 |
| Example 21 | Included | 99.92 | 99.90 | 99.91 | 99.80 | 99.54 |

As is apparent from Table 75, the intact heavy-chain and light-chain content was higher in Example 21 than in Comparative Example 3 after 4 weeks at 40° C.

Whether or not Metal Salts are Included

Turbidity

TABLE 76

| Classification | Whether or not sugar or salts are included | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Comparative Example 5 | Including sodium chloride | 0.0555 | 0.0596 | 0.0629 | 0.0575 | 0.0634 |
| Example 21 | Including sorbitol | 0.0020 | 0.0046 | 0.0044 | 0.0030 | 0.0039 |

As is apparent from Table 76, the absorbance of Comparative Example 5 under all conditions of 5° C. and 40° C. was 0.05 or more, which was evaluated to be very high compared to Example 21.

High-Molecular-Weight Component Content

TABLE 77

| Classification | Whether or not sugar or salts are included | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Comparative Example 5 | Including sodium chloride | 0.6 | 0.6 | 1.2 | 0.6 | 1.6 |
| Example 21 | Including sorbitol | 0.5 | 0.5 | 0.9 | 0.7 | 1.2 |

As is apparent from Table 77, the high-molecular-weight component content was higher in Comparative Example 5 than in Example 21 after 4 weeks at 5° C. and 40° C.

Main Component Content

TABLE 78

| Classification | Whether or not sugar or salts are included | After 0 weeks at 5 ± 3° C. | After 2 weeks at 5 ± 3° C. | After 4 weeks at 5 ± 3° C. | After 2 weeks at 40 ± 2° C. | After 4 weeks at 40+2° C. |
|---|---|---|---|---|---|---|
| Comparative Example 5 | Including sodium chloride | 99.3 | 99.3 | 98.2 | 99.2 | 97.4 |
| Example 21 | Including sorbitol | 99.4 | 99.4 | 98.6 | 99.2 | 97.9 |

As is apparent from Table 78, the main component content was lower in Comparative Example 5 than in Example 21 after 4 weeks at 5° C. and 40° C.

Low-Molecular-Weight Component Content

TABLE 79

| Classification | Whether or not sugar or salts are included | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Comparative Example 5 | Including sodium chloride | 0.1 | 0.1 | 0.6 | 0.2 | 1.1 |
| Example 21 | Including sorbitol | 0.1 | 0.1 | 0.5 | 0.2 | 0.9 |

As is apparent from Table 79, the low-molecular-weight component content was higher in Comparative Example 5 than in Example 21 after 4 weeks at 5° C. and 40° C.

Intact Immunoglobulin G Content (Intact IgG %)

TABLE 80

| Classification | Whether or not sugar or salts are included | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Comparative Example 5 | Including sodium chloride | 98.9 | 98.2 | 97.0 | 97.1 | 94.2 |
| Example 21 | Including sorbitol | 99.0 | 98.1 | 97.4 | 97.0 | 95.0 |

As is apparent from Table 80, the intact immunoglobulin G content was lower in Comparative Example 5 than in Example 21 after 4 weeks at 5° C. and 40° C.

Oxidation Rate (Heavy-Chain Met 255)

TABLE 81

| Classification | Whether or not sugar or salts are included | After 0 weeks at 5 ± 3° C. | After 4 weeks at 5 ± 3° C. | After 4 weeks at 40 ± 2° C. |
|---|---|---|---|---|
| Comparative Example 5 | Including sodium chloride | 2.9 | 3.0 | 3.8 |
| Example 21 | Including sorbitol | 2.7 | 2.6 | 2.9 |

As is apparent from Table 81, the oxidation rate was higher in Comparative Example 5 than in Example 21 after 4 weeks at 5° C. and 40° C.

Subvisible Particles (10.00 μm≤, <100.00 μm)

TABLE 82

| Classification | Whether or not sugar or salts are included | After 0 weeks at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|---|
| Comparative Example 5 | Including sodium chloride | 0 | 13 | 25 | 7 | 2120 |
| Example 21 | Including sorbitol | 5 | 0 | 7 | 5 | 162 |

As is apparent from Table 82, the number of subvisible particles (10.00 μm≤, <100.00 μm) was much higher in Comparative Example 5 than in Example 21 after 4 weeks at 5° C. and 40° C.

Experimental Example 5: Comparison of Stability Depending on Concentration of Additional Antibody Regarding the liquid pharmaceutical formulations used in Experimental Example 5, an additional experiment was performed in order to evaluate changes in the stability of the formulation depending on changes in the concentration of the antibody. To this end, each buffer solution was prepared at a pH of 5.0 using sodium acetate and added with sorbitol as a sugar alcohol, thus yielding the samples set forth in Table 83 below. The content of each component was as described in Table 83 below. The total volume was 3 mL.

TABLE 83

| Classification | Antibody content (mg/mL) | Surfactant | Sugar/Salts | Buffer solution | pH | Amino acid |
|---|---|---|---|---|---|---|
| Example 22 | 10 | Polysorbate 80 0.05% (w/v) | Sorbitol 4.5% (w/v) | Sodium acetate 25 mM | 5.0 | Methionine 10 mM |
| Example 23 | 50 | Polysorbate 80 0.05% (w/v) | Sorbitol 4.5% (w/v) | Sodium acetate 25 mM | 5.0 | Methionine 10 mM |
| Example 24 | 120 | Polysorbate 80 0.05% (w/v) | Sorbitol 4.5% (w/v) | Sodium acetate 25 mM | 5.0 | Methionine 10 mM |

The above formulations were measured for stability after 0 weeks and 2 weeks at a temperature of 5±3° C., and for stability after 2 weeks at a temperature of 40±2° C. and a relative humidity of 75±5%. The results thereof are shown in Tables 84 to 90 below.

Concentration of Antibody

Turbidity

TABLE 84

| Classification | Antibody content (mg/mL) | After 0 weeks at 5 ± 3° C. | After 2 weeks at 5 ± 3° C. | After 2 weeks at 40 ± 2° C. |
|---|---|---|---|---|
| Example 22 | 10 | 0.0034 | 0.0014 | 0.0031 |
| Example 23 | 50 | 0.0033 | 0.0028 | 0.0033 |
| Example 24 | 120 | 0.0037 | 0.0037 | 0.0067 |

As is apparent from Table 84, the absorbance was generally low, specifically 0.0070 or less, after 2 weeks at 5° C. and 40° C. within the antibody content range of 10 mg/ml to 120 mg/ml.

High-Molecular-Weight Component Content

TABLE 85

| Classification | Antibody content (mg/mL) | After 0 weeks at 5 ± 3° C. | After 2 weeks at 5 ± 3° C. | After 2 weeks at 40 ± 2° C. |
|---|---|---|---|---|
| Example 22 | 10 | 0.37 | 0.48 | 0.43 |
| Example 23 | 50 | 0.43 | 0.56 | 0.57 |
| Example 24 | 120 | 0.46 | 0.59 | 0.85 |

As is apparent from Table 85, the high-molecular-weight component content increased with an increase in the antibody concentration, but the high-molecular-weight component content was generally low after 2 weeks at 5° C. and 40° C. within the antibody concentration range of 10 to 120 mg/mL.

Main Component Content

TABLE 86

| Classification | Antibody content (mg/mL) | After 0 weeks at 5 ± 3° C. | After 2 weeks at 5 ± 3° C. | After 2 weeks at 40 ± 2° C. |
|---|---|---|---|---|
| Example 22 | 10 | 99.46 | 99.37 | 99.15 |
| Example 23 | 50 | 99.40 | 99.31 | 98.98 |
| Example 24 | 120 | 99.38 | 99.27 | 98.64 |

As is apparent from Table 86, the main component content decreased with an increase in the antibody concentration, but the main component content was generally high after 2 weeks at 5° C. and 40° C. within the antibody concentration range of 10 to 120 mg/mL.

Low-Molecular-Weight Component Content

TABLE 87

| Classification | Antibody content (mg/mL) | After 0 weeks at 5 ± 3° C. | After 2 weeks at 5 ± 3° C. | After 2 weeks at 40 ± 2° C. |
|---|---|---|---|---|
| Example 22 | 10 | 0.18 | 0.14 | 0.43 |
| Example 23 | 50 | 0.17 | 0.14 | 0.45 |
| Example 24 | 120 | 0.16 | 0.14 | 0.50 |

As is apparent from Table 87, the low-molecular-weight component content was generally low after 2 weeks at 5° C. and 40° C. within the antibody concentration range of 10 to 120 mg/mL.

Intact Immunoglobulin G Content (Intact IgG %)

TABLE 88

| Classification | Antibody content (mg/mL) | After 0 weeks at 5 ± 3° C. | After 2 weeks at 5 ± 3° C. | After 2 weeks at 40 ± 2° C. |
|---|---|---|---|---|
| Example 22 | 10 | 99.69 | 97.74 | 96.80 |
| Example 23 | 50 | 99.66 | 97.78 | 96.82 |
| Example 24 | 120 | 99.67 | 97.75 | 96.67 |

As is apparent from Table 88, the intact immunoglobulin G content was generally high after 2 weeks at 5° C. and 40° C. within the antibody concentration range of 10 to 120 mg/mL.

Intact Heavy-Chain and Light-Chain Content (Intact HC+LC %)

TABLE 89

| Classification | Antibody content (mg/mL) | After 0 weeks at 5 ± 3° C. | After 2 weeks at 5 ± 3° C. | After 2 weeks at 40 ± 2° C. |
|---|---|---|---|---|
| Example 22 | 10 | 99.95 | 99.75 | 99.63 |
| Example 23 | 50 | 99.94 | 99.75 | 99.63 |
| Example 24 | 120 | 99.95 | 99.74 | 99.63 |

As is apparent from Table 89, the intact heavy-chain and light-chain content was generally high after 2 weeks at 5° C. and 40° C. within the antibody concentration range of 10 to 120 mg/mL.

Oxidation Rate (Heavy-Chain Met 255)

TABLE 90

| Classification | Antibody content (mg/mL) | After 0 weeks at 5 ± 3° C. | After 2 weeks at 5 ± 3° C. | After 2 weeks at 40 ± 2° C. |
|---|---|---|---|---|
| Example 22 | 10 | 3.4 | 3.4 | 3.4 |
| Example 23 | 50 | 3.7 | 3.4 | 3.5 |
| Example 24 | 120 | 3.9 | 3.5 | 3.6 |

As is apparent from Table 90, the oxidation rate of heavy-chain Met 255 was generally low, specifically 3.9% or less, after 2 weeks at 5° C. and 40° C. within the antibody concentration range of 10 to 120 mg/mL.

The invention claimed is:

1. A stable liquid pharmaceutical formulation, comprising:
   (A) an antibody or antigen-binding fragment thereof;
   (B) a surfactant;
   (C) a sugar or a sugar derivative;
   (D) a buffer; and
   (E) a stabilizer; wherein
   (A) the antibody comprises an antibody that binds to HER2;
   a concentration of (A) the antibody or antigen-binding fragment thereof is 250 mg/ml or less; and
   the stable liquid pharmaceutical formulation does not comprise histidine.

2. The stable liquid pharmaceutical formulation of claim 1, wherein (A) the antibody comprises trastuzumab, pertuzumab, or a mixture thereof.

3. The stable liquid pharmaceutical formulation of claim 1, wherein (A) the antibody comprises a humanized IgG monoclonal antibody.

4. The stable liquid pharmaceutical formulation of claim 1, wherein (A) the antibody or antigen-binding fragment thereof comprises:
   a light-chain variable region comprising a CDR1 domain comprising an amino acid sequence of SEQ ID NO:1, a CDR2 domain comprising an amino acid sequence of SEQ ID NO:2, and a CDR3 domain comprising an amino acid sequence of SEQ ID NO:3; and
   a heavy-chain variable region comprising a CDR1 domain comprising an amino acid sequence of SEQ ID NO:4, a CDR2 domain comprising an amino acid sequence of SEQ ID NO:5, and a CDR3 domain comprising an amino acid sequence of SEQ ID NO:6.

5. The stable liquid pharmaceutical formulation of claim 1, wherein (A) the antibody or antigen-binding fragment thereof comprises a light-chain variable region comprising an amino acid sequence of SEQ ID NO:7 and a heavy-chain variable region comprising an amino acid sequence of SEQ ID NO:8.

6. The stable liquid pharmaceutical formulation of claim 1, wherein (A) the antibody comprises a light chain comprising an amino acid sequence of SEQ ID NO:9 and a heavy chain comprising an amino acid sequence of SEQ ID NO:10.

7. The stable liquid pharmaceutical formulation of claim 1, wherein (B) the surfactant comprises polysorbate, poloxamer or a mixture thereof.

8. The stable liquid pharmaceutical formulation of claim 1, wherein (B) the surfactant comprises Polysorbate 20, Polysorbate 40, Polysorbate 60, Polysorbate 80, or a mixture of two or more thereof.

9. The stable liquid pharmaceutical formulation of claim 1, wherein (B) the surfactant comprises Polysorbate 80.

10. The stable liquid pharmaceutical formulation of claim 1, wherein a concentration of (B) the surfactant is 0.02 to 0.1% (w/v).

11. The stable liquid pharmaceutical formulation of claim 1, wherein (C) the sugar comprises a monosaccharide, a disaccharide, an oligosaccharide, a polysaccharide, or a mixture of two or more thereof, and (C) the sugar derivative comprises a sugar alcohol, a sugar acid, or a mixture thereof.

12. The stable liquid pharmaceutical formulation of claim 1, wherein (C) the sugar or the sugar derivative comprises sorbitol, mannitol, trehalose, sucrose, or a mixture of two or more thereof.

13. The stable liquid pharmaceutical formulation of claim 1, wherein a concentration of (C) the sugar or the sugar derivative is 1 to 10% (w/v).

14. The stable liquid pharmaceutical formulation of claim 1, wherein (D) the buffer comprises acetate.

15. The stable liquid pharmaceutical formulation of claim 1, wherein a content of (D) the buffer is 1 to 50 mM.

16. The stable liquid pharmaceutical formulation of claim 1, wherein (E) the stabilizer comprises methionine, aspartic acid, proline, or a mixture of two or more thereof.

17. The stable liquid pharmaceutical formulation of claim 1, wherein (E) the stabilizer comprises methionine.

18. The stable liquid pharmaceutical formulation of claim 1, wherein a content of (E) the stabilizer is 5 to 100 mM.

19. The stable liquid pharmaceutical formulation of claim 1, having a pH of 4.5 to 6.0.

20. The stable liquid pharmaceutical formulation of claim 1, which does not comprise NaCl, KCl, NaF, KBr, NaBr, $Na_2SO_4$, NaSCN, $K_2SO_4$, or a mixture thereof.

21. The stable liquid pharmaceutical formulation of claim 1, comprising:
  (A) 250 mg/ml or less of an antibody or antigen-binding fragment thereof comprising a light-chain variable region comprising a CDR1 domain comprising an amino acid sequence of SEQ ID NO:1, a CDR2 domain comprising an amino acid sequence of SEQ ID NO:2, and a CDR3 domain comprising an amino acid sequence of SEQ ID NO:3, and a heavy-chain variable region comprising a CDR1 domain comprising an amino acid sequence of SEQ ID NO:4, a CDR2 domain comprising an amino acid sequence of SEQ ID NO:5, and a CDR3 domain comprising an amino acid sequence of SEQ ID NO:6;
  (B) 0.02 to 0.1% (w/v) of a surfactant;
  (C) 1 to 10% (w/v) of a sugar or a sugar derivative;
  (D) 1 to 50 mM of a buffer; and
  (E) 5 to 100 mM of a stabilizer.

22. A method for administration of the stable liquid pharmaceutical formulation of claim 1, comprising:
  administering to a subject the stable liquid pharmaceutical formulation by intravenous administration or subcutaneous administration.

23. The stable liquid pharmaceutical formulation of claim 1, which does not undergo either or both of a reconstitution step and a dilution step before use.

24. A pre-filled syringe filled with the stable liquid pharmaceutical formulation of claim 1.

25. An auto-injector comprising therein the pre-filled syringe of claim 24.

* * * * *

SEQUENCE LISTING

```
<160> NUMBER OF SEQ ID NOS: 10

<210> SEQ ID NO 1
<211> LENGTH: 11
<212> TYPE: PRT
<213> ORGANISM: Artificial Sequence
<220> FEATURE:
<223> OTHER INFORMATION: Antibody

<400> SEQUENCE: 1

Arg Ala Ser Gln Asp Val Asn Thr Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CDR2 domain

<400> SEQUENCE: 2
```

Ser Ala Ser Phe Leu Tyr Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Antibody

<400> SEQUENCE: 3

Gln Gln His Tyr Thr Thr Pro Pro Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Antibody

<400> SEQUENCE: 4

Gly Phe Asn Ile Lys Asp Thr Tyr Ile His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Antibody

<400> SEQUENCE: 5

Arg Ile Tyr Pro Thr Asn Gly Tyr Thr Arg Tyr Ala Asp Ser Val Lys
1               5                   10                  15

Gly

<210> SEQ ID NO 6
<211> LENGTH: 11
<212> TYPE: PRT
<213> ORGANISM: Artificial Sequence
<220> FEATURE:
<223> OTHER INFORMATION: Antibody

<400> SEQUENCE: 6

Trp Gly Gly Asp Gly Phe Tyr Ala Met Asp Tyr
1               5                   10

<210> SEQ ID NO 7
<211> LENGTH: 107
<212> TYPE: PRT
<213> ORGANISM: Artificial Sequence
<220> FEATURE:
<223> OTHER INFORMATION: Antibody

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 8
<211> LENGTH: 120
<212> TYPE: PRT
<213> ORGANISM: Artificial Sequence
<220> FEATURE:
<223> OTHER INFORMATION: Antibody

<400> SEQUENCE: 8

Glu Val Gln Leu Val Glu Ser Gly Gly Leu Val Gln Pro Gly Gly
 1               5                   10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 9
<211> LENGTH: 216
<212> TYPE: PRT
<213> ORGANISM: Artificial Sequence
<220> FEATURE:
<223> OTHER INFORMATION: Antibody

<400> SEQUENCE: 9

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
 130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Tyr Glu Lys His Lys
        180                 185                 190

Val Tyr Ala Cys Glu Val Thr His Gln Gly Leu Ser Ser Pro Val Thr
            195                 200                 205

Lys Ser Phe Asn Arg Gly Glu Cys
        210                 215

<210> SEQ ID NO 10
<211> LENGTH: 450
<212> TYPE: PRT
<213> ORGANISM: Artificial Sequence
<220> FEATURE:
<223> OTHER INFORMATION: Antibody

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290             295                 300

Val Val Ser Val Leu Thr Val Leu His Gln Asp Trp Leu Asn Gly Lys
305             310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```